United States Patent [19]

Cano et al.

[11] Patent Number: 5,209,228
[45] Date of Patent: May 11, 1993

[54] ELECTRONIC PACEMAKER TESTING DEVICE

[75] Inventors: Gerald G. Cano; Douglas A. Coast; Mark A. Lubinski; Frederick W. Moeller; Timothy E. Rapp, all of Pittsburgh, Pa.

[73] Assignee: Allegheny-Singer Research Institute, Pittsburgh, Pa.

[21] Appl. No.: 605,851

[22] Filed: Oct. 26, 1990

[51] Int. Cl.⁵ .............................................. A61N 1/37
[52] U.S. Cl. ............................................ 128/419 PT
[58] Field of Search ................................ 128/419 PT

[56] References Cited

U.S. PATENT DOCUMENTS

| | | | |
|---|---|---|---|
| 3,757,790 | 9/1973 | Herrmonn | 128/419 PT |
| 3,865,119 | 2/1975 | Svensson et al. | 128/419 |
| 3,871,363 | 3/1975 | Day | 128/2.06 |
| 3,920,005 | 11/1975 | Gombrich et al. | 128/2.06 |
| 4,021,736 | 5/1977 | Walters et al. | 324/181 |
| 4,141,367 | 2/1979 | Ferreira | 128/419 PT |
| 4,142,533 | 3/1979 | Brownlee et al. | 128/419 |
| 4,156,430 | 5/1979 | King et al. | 128/419 |
| 4,256,114 | 3/1981 | Carlson et al. | 128/419 |
| 4,263,548 | 4/1981 | Carlson et al. | 324/102 |
| 4,290,430 | 9/1981 | Bihn et al. | 128/419 PT |
| 4,295,468 | 10/1981 | Bartelt | 128/419 |
| 4,640,285 | 2/1987 | DeCote, Jr. et al. | 128/419 PT |
| 4,705,042 | 11/1987 | Giurtino | 128/419 |

OTHER PUBLICATIONS

"An External Demand Pacemaker Evaluation System", Coiro, Daniel J. Journal of Clinical Engineering, vol. 14, No. 1, Jan.-Feb. 1989.
"External (Transvenous) Cardiac Pacemakers" Procedure/Checklist No. 418-484 (Apr. 1984).
Environics Adaptive Technology brochure re "QUIK-CHEK ™".
Medtronic 5311 A-V Pacing System Analyzer Technical Manual.

Primary Examiner—William E. Kamm
Attorney, Agent, or Firm—Webb, Burden, Ziesenheim & Webb

[57] ABSTRACT

An electronic test instrument for rapid comprehensive verification of correct operation of medical pacers. This portable microprocessor-based test instrument includes a device for measuring and displaying pacer characteristics including pacing rate, pulse duration, pulse amplitude, sensitivity, sensed refractory interval, stimulus refractory interval, atrio-ventricular delay, D.C. leakage, susceptibility to A.C. interference, frequency response and battery drain. The test instrument includes a device for selecting each test and entering associated parameters, a device to convert the analog pacer pulses to digital values for detection and measurement, a device to generate variable amplitude test waveforms and apply them to a medical pacer at a specified rate or at a specified delay from a previous pacer pulse or with a specified delay between two test waveforms and a device for displaying test results. Sensed and stimulus refractory intervals are determined in minimal time using a unique binary search strategy which continually halves the range of possible refractory intervals until the desired interval is determined.

14 Claims, 14 Drawing Sheets

ELECTRONIC PACEMAKER TESTING DEVICE

BACKGROUND OF THE INVENTION

1. Field of the Invention

The present invention pertains generally to a device and a method for verifying correct operation (safety testing) of medical pacer (also known as "pacemaker") devices. The present invention pertains more particularly to a method and a device for testing pacemakers utilizing a portable self-contained microcomputer-based pacemaker testing device capable of performing comprehensive safety testing of pacemakers at any desired location, eliminating the prior art need for complex and expensive additional testing equipment, which further provides a significant reduction in the amount of time necessary to comprehensively test the pacemakers.

2. Description of the Prior Art

Medical pacing equipment can be generally divided into two types, that which is implanted internally into the body, and that which is maintained externally to the body. While the present invention can be modified to test all types of medical pacing equipment, the present invention is particularly well-suited to the testing of external medical pacing equipment, and is most particularly well-suited to the testing of external cardiac pacemakers.

A specific type of medical pacer is the cardiac pacemaker. Cardiac pacemakers are devices that provide an electrical stimulus to the heart muscle at regular intervals. Application of the stimuli is through appropriate lead wires and electrodes causing the heart muscle to contract. Cardiac pacemakers can be either implanted internally within the body or utilized externally to the body.

External cardiac pacing is routinely employed in hospitals to temporarily alleviate cardiac dysfunction following trauma, heart attack, major surgery or until a permanent pacemaker can be implanted.

Two common types of external cardiac pacemakers are the ventricular demand and atrio-ventricular sequential demand type pacemakers. The first is designed to generate stimuli that are applied to the ventricles of the heart (ventricular external demand pacemakers) causing the ventricles to contract. The second type of cardiac pacemaker is designed to generate two sequential stimuli, one applied to the atria and the other applied to the ventricles so that these contract in sequence (atrio-ventricular (A-V) sequential external demand pacemakers).

As with all clinical instrumentation, external cardiac pacemakers must be routinely checked as a safety precaution in order to assure proper performance and calibration. This responsibility is borne by the clinical engineering department in a typical health care facility.

The testing of external cardiac pacemakers may be generally separated into two types of testing, a relatively quick operational test that is performed on a regular basis, and a more comprehensive detailed testing procedure that is also performed on a regular, though less frequent, basis.

The testing of external cardiac pacemakers must be carefully performed, and the Emergency Care Research Institute (ECRI), an established advisor to the medical profession, has established recommended safety and performance standards for external pacemakers. Additionally, the manufacturers of external cardiac pacemakers also often provide "checkout manuals" for their external pacemaker products which specify the necessary test procedures for verifying both programmable and fixed parameters.

Although it may be subject to change from time to time, one recommended external cardiac pacemaker comprehensive testing procedure comprises a battery of tests including, but not limited to: 1) pulse duration; 2) pulse amplitude; 3) pulse rate; 4) sensitivity; 5) rate compensation; 6) refractory intervals (stimulus and sensed); and where the pacemaker is an atrio-ventricular sequential pacemaker, 7) atrio-ventricular (A-V) delay intervals. In an A-V sequential pacemaker, the first six tests are measured for each of the atrial and ventricular stimulation circuitries; the seventh test measures timing between atrial and ventricular pacing pulses. Additionally, the following tests can also be performed if deemed necessary at the discretion of the operator performing the tests: 8) ventricular and/or atrial direct current (D.C.) leakage; 9) alternating current (A.C.) interference test; 10) battery drain test; and, 11) ventricular frequency response test. These tests are discussed in greater detail below.

Implementing either of the above testing procedures the ECRI procedures or the manufacturer's procedures is a very time consuming process requiring several pieces of testing equipment, including a function generator, oscilloscope, and multimeter. Comprehensive testing of an external cardiac pacemaker under these conditions requires that the pacemaker be returned to the clinical engineering laboratory and generally requires at least an hour and a half of testing time per pacemaker.

Attempts have been made in the art to improve the ease and efficiency of testing cardiac pacemakers. However, these attempts have been for the most part directed only to limited as opposed to comprehensive testing and have been generally limited to implantable type cardiac pacemakers.

For example, the prior art includes several separate systems designed to test either only individual parameters of cardiac pacemakers or discrete circuits. Examples include: U.S. Pat. No. 4,021,736, issuing May 3, 1977 to Walters et al. directed to a circuit for measuring the refractory period; U.S. Pat. No. 4,256,114, issuing Mar. 17, 1981 to Carlson et al. also directed to measuring refractory intervals; U.S. Pat. No. 4,263,548, issuing Apr. 21, 1981 to Bartelt et al. directed to measuring amplitude; and U.S. Pat. No. 4,295,468, issuing Oct. 20, 1981 to Bartelt directed to measuring R wave sensitivity. While these advances in the art may have improved the evaluation of pacemakers, they have not provided for a means to comprehensively and expeditiously test pacemakers outside of the laboratory setting.

Daniel J. Coiro, "An External Demand Pacemaker Evaluation System", *Journal of Clinical Engineering*, Vol. 14, No. 1, pp. 49-54 (1989), describes a test device to facilitate the evaluation of external demand pacemakers. Coiro's device eliminates some of the additional circuitry needed, but still requires an oscilloscope and is not easily portable.

A portable pacemaker testing device is available from Environics Adaptive Technology, Inc., of Newton, Mass., under the "QUICK-CHEK" TM mark. However, this device is capable of performing only superficial testing and does not provide a full evaluation of an external pacemaker as specified by the manufacturers of many pacemakers or by ECRI.

Environics Adaptive Technology, Inc. also markets a personal computer-based external pacemaker analyzer under the mark PACE-ALYZER ™. This product consists of an add-on card for a personal computer, and associated software under the mark PACE-SOFT ™. However, this product is not self-contained or portable, does not perform all of the tests necessary to comprehensively test medical pacing units, and requires the user to obtain and incur the additional expense of the necessary personal computer which in most applications is not battery-powered or portable.

Thus, a need exists in the art for a portable, self-contained comprehensive medical pacer testing device that expedites the complete analysis of all critical medical pacer parameters.

There also exists a need in the art for medical pacer testing devices which permit the analysis of all critical medical pacer parameters in clinical care or other settings in order to eliminate the need to return the pacer to the laboratory for comprehensive testing.

SUMMARY OF THE INVENTION

It is an object of the present invention to provide a method and a device for the comprehensive testing of medical pacers in general, and external cardiac pacemakers in particular, utilizing a portable self-contained microcomputer-based pacemaker testing device (alternatively described as a medical pacing unit tester) capable of performing comprehensive safety testing of pacemakers at any desired location, eliminating the prior art need for complex and expensive additional testing equipment. It is a further object of the present invention to provide a significant reduction in the amount of time necessary to comprehensively test the pacemakers.

In one embodiment, the medical pacer testing device of the present invention is a microprocessor-based instrument which provides a numeric readout of measured parameters. One or more of the battery of comprehensive tests are selected by a data entry device, which in a preferred embodiment is a 12-key numeric or alpha/numeric keypad. Preset medical pacer parameters can also be inputted through the data entry device.

In order to perform the actual testing of the medical pacer, two ventricular sense/control lines of the testing device are connected to a pair of terminals or jacks on the pacemaker.

If the pacemaker is an A-V sequential pacemaker, the atrial sense/control lines of the testing device are connected to another pair of terminals or jacks on the pacemaker.

Where a particular test first requires that a test waveform be sent to the pacemaker, the testing device transmits the test waveform (including by way of example, but not limited to simulated P waves corresponding to those generated by the atria, and/or R waves which correspond to those generated by the ventricles) to the pacemaker. Specifically, software creates a digitized version of the P wave and R wave and outputs the simulated wave as a signal after it is converted via a digital-to-analog (D/A) converter at the proper (correct) interval from the current pulses generated by the pacemaker.

Similarly, current pulses transmitted by the pacemaker are converted to a proportional voltage; and these signals are digitized by an analog-to-digital (A/D) converter for input into the testing device.

The testing device analyzes the now digitized signals received from the medical pacer. A timing device associated with and/or part of the testing device provides the necessary time measurement of signals received and/or generated by the testing device.

Upon completion of its analysis, the testing device displays the testing results as a one, two or three digit number along with the proper units of measurement on an appropriately designed display. The operator can also choose whether to store the test results in the memory of the testing device for future recall and/or download those results to a printing device for hardcopy when desired.

Thus, the aforementioned and other objects are accomplished in accordance with the present invention which in one embodiment provides a self-contained, portable medical pacer testing device capable of quickly and comprehensively testing medical pacers comprising:

(a) a means for transferring signals between said tester and said medical pacing unit which is being tested by said tester;

(b) a data entry device, said data entry device further comprising a means to select one or more medical pacing unit tests and to input one or more medical pacing unit parameters where said parameters are necessary to perform said selected medical pacing unit tests;

(c) a means for timing intervals associated with performing said pacing unit tests;

(d) a means to generate a first set of test signals to be sent to said pacing unit when required for one of said medical pacing unit tests, said means for generating said first set of test signals further comprising a microcomputer and necessary memory and a digital/analog converter;

(e) a means to analyze a second set of pacing signals received by said tester from said pacing unit, said second set of pacing signals either being generated by said pacing unit pursuant to previously input programming, or alternatively generated by said pacing unit in response to said first set of test signals, said means to analyze further comprising a microcomputer and an analog/digital converter; and (f) a means to display the result(s) of said analysis.

DETAILED DESCRIPTION OF THE INVENTION

The pacemaker testing device described herein is especially suitable for comprehensive testing of medical pacers generally, and external cardiac pacemakers specifically. More particularly, the present invention is especially designed for measuring fixed and variable parameters of external ventricular demand pacemakers and external atrio-ventricular (A-V) sequential demand pacemakers. The testing device includes a device for sensing the output pulses generated by a pacemaker as well as means for presenting test waveforms to the pacemaker.

Figure 1:
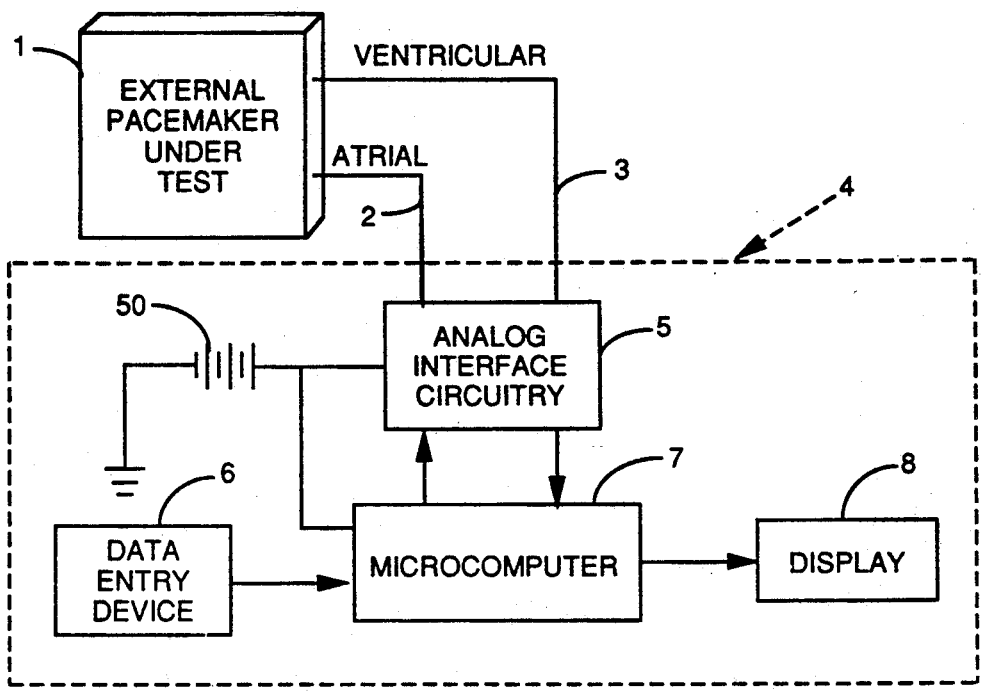
FIG. 1 is a block diagram of one embodiment of a pacemaker testing device in accordance with the present invention showing the major components of a pacemaker testing device including the connection of the pacemaker testing device to an external pacemaker.

Referring now to FIG. 1, a block diagram is provided of one embodiment of the testing device in accordance with the present invention. The testing device 4 is a portable self-contained device comprising microcomputer 7, analog interface circuitry 5, data entry device 6, and display 8.

Data entry device 6 can be any device capable of permitting the operator to select one or more of the comprehensive battery of tests, and which also permits the operator to input related numerical test parameters, if applicable, of the pacemaker 1 which is being tested. The preferred embodiment of data entry device 6 is a keypad. One example is model 83AA1-101 keypad, available from Grayhill, Inc. of LaGrange, Ill. The most preferred embodiment of data entry device 6 is a 12-key numeric or alpha/numeric keypad.

By self-contained it is meant that the testing device 4 contains all of the equipment necessary to comprehensively test pacemaker 1, and that no additional testing equipment is necessary to perform comprehensive testing of pacemaker 1, including but not limited to function generators, oscilloscopes and/or multimeters.

Testing device 4 must, of course, have access to a power source. The power source can be either alternating or direct current. As shown in FIG. 1, the power source can also be supplied from battery 50. Battery power is the preferred power source as it increases the portability of the unit. The selection of the particular type of battery power is not critical to the present invention, and can be either a rechargeable or disposable battery source. In a preferred embodiment of the present invention, a rechargeable battery source supplies power to the testing device 4, and testing device 4 further includes an indicator of the type known in the art to indicate when the battery or batteries powering testing device 4 need to be recharged.

Numerical test results are displayed on display 8. In a preferred embodiment of the present invention, display 8 includes annunciators indicating which test has been selected as well as the appropriate units associated with the test results. While any type of display known in the art which is compatible with microcomputer 7 may be used in the present invention, where battery power is the power source, a liquid crystal display is preferred in order to increase battery life. One example is model 0068 display, available from Hamlin, Inc. of Lake Mills, Wis. Most preferred with the present invention is a three digit liquid crystal display.

Connections are made from ventricular output terminals 3 (and from atrial output terminals 2 where pacemaker 1 is an A-V sequential pacemaker) of testing device 4 to the appropriate terminals of pacemaker 1. For ventricular pacemakers connection 2 is not utilized. The purpose of the connections is to provide a means for transferring signals between testing device 4 and pacemaker 1, and any suitable connections known in the art which fulfill this purpose will do.

The testing device 4 incorporates analog interface circuitry 5 to convert pacemaker 1 output pulses into digital representations which are then detected and measured by microcomputer 7. Analog interface circuitry 5 also converts digital values generated by testing device 4 to analog test waveforms which are applied to pacemaker 1 through atrial output terminals 2 and ventricular output terminals 3.

Figure 2:
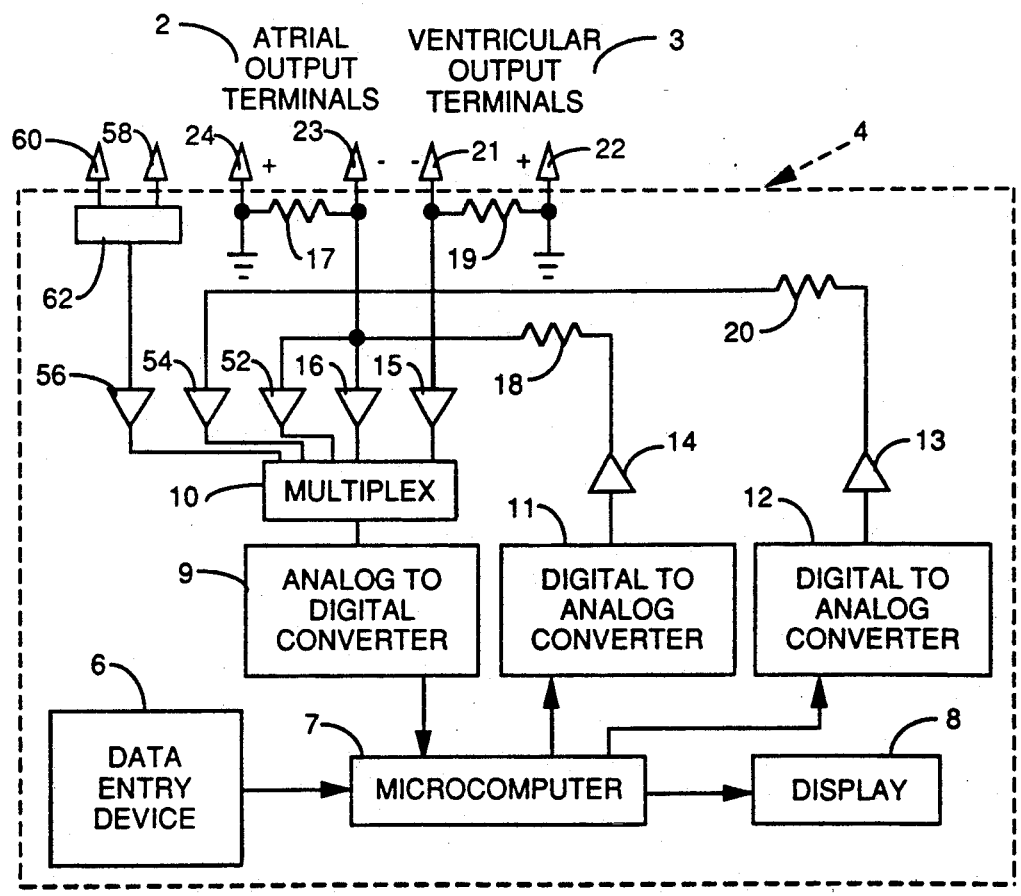
FIG. 2 is a block diagram of one embodiment of a pacemaker testing device in accordance with the present invention showing a more detailed representation of the analog interface circuitry.

Referring now to FIG. 2, the analog interface circuitry 5 in accordance with one embodiment of the present invention is shown in greater detail. Ventricular output terminals 3 of pacemaker 1 are connected to negative ventricular terminal 21 and positive ventricular terminal 22 of testing device 4.

(Where pacemaker 1 is an A-V sequential pacemaker, atrial output terminals 2 of pacemaker 1 are also connected to negative atrial terminal 23 and positive atrial terminal 24 of testing device 4. For the remainder of the discussion it will be assumed that pacemaker 1 is an A-V sequential pacemaker, although it is clear from the foregoing that if pacemaker 1 were a ventricular pacemaker, the atrial discussion would simply be omitted.)

Load resistors 17 and 19 are connected between positive and negative terminals 24, 23 of the atrial and 22, 21 ventricular terminals respectively, as shown in FIG. 2. In the preferred embodiment, resistance value for load resistors 17 and 19 is approximately 500 ohms.

The following discussion describes the process of converting pacing pulses generated by pacemaker 1 from an analog waveform to a series of digital values for input to microcomputer 7. By way of example, this discussion describes the conversion of atrial and ventricular pacing pulses generated by pacemaker 1, though it is to be understood that this process would be the same for any analog waveform generated by pacemaker 1.

In operation, an atrial pacing pulse generated by pacemaker 1 flows between terminals 23 and 24 and appears as a voltage pulse across load resistor 17. This voltage pulse is attenuated and inverted by inverting amplifier 16 and then passes through multiplexer 10 to analog-to-digital converter 9 where the voltage pulse is sampled and converted to a digital value.

Similarly, in operation a ventricular pacing pulse generated by pacemaker 1 flows between terminals 21 and 22 and is similarly converted to a voltage pulse across load resistor 19, attenuated and inverted by inverting amplifier 15, and passes through multiplexer 10 to analog-to-digital converter 9 where the voltage pulse is likewise sampled and converted to a digital value. An example of an amplifier compatible with the present invention for inverting amplifiers 15 or 16 is a model TLC27L9 available from Texas Instruments, Inc. of Dallas, Tex.

Still referring to FIG. 2, the direct current (D.C.) circuitry necessary to measure D.C. leakage in accordance with one embodiment of the present invention is shown. To measure D.C. leakage current from either the atrial or ventricular leads (which results in voltages of only a few millivolts across load resistors 17 or 19), amplifiers with voltage gains of approximately 100 are required. Inverting amplifiers 52 and 54 are provided to measure direct current leakage current flowing through load resistors 17 and 19, respectively. Amplifiers 52 and 54 are connected to multiplexer 10 thus allowing D.C. leakage current to be measured by selecting the corresponding multiplexer channel and converting the proportional voltage to a digital value using analog-to-digital converter 9. To measure pacemaker battery current drain, the negative pacemaker battery connection is removed from the negative battery terminal and connected instead to terminal 58 of the testing device; a connection is then made from terminal 60 of the testing device to the negative battery terminal. Thus the battery current supplied to the pacemaker passes through circuit 62 connected between terminals 58 and 60. Circuit 62 converts this current to a proportional voltage using an isolating analog amplifier comprised of a pair of matched optoisolators. An isolating analog amplifier is required since no common ground reference between pacemaker 1 and testing device 4 is available. The proportional voltage from circuit 62 passes through amplifier 56 to an input channel of multiplexer 10, and then to analog-to-digital converter 9. An example of an amplifier compatible with the present invention for amplifiers 52, 54 and 56 is a model TLC27L9 available from Texas Instruments, Inc. of Dallas, Tex. An example of dual optoisolators compatible with the design of isolating analog amplifier 62 is model MCT6 available from General Instruments Corporation of Palo Alto, Calif.

The function of multiplexer 10 in the foregoing is to sequence the input into analog-to-digital converter so that only one analog-to-digital converter is needed. In a preferred embodiment, both analog-to-digital converter 9 and multiplexer 10 are included as part of microcomputer 7 as part of microprocessor 25.

These digital values are sent to microcomputer 7 which analyzes the digital signals pursuant to the specific test selected, transferring the test results to display 10, where the results are observed by the person conducting the test of pacemaker 1.

For certain of the tests in the comprehensive battery of tests, test signals or waveforms must first be generated by testing device 4 and transferred to pacemaker 1, whereupon pacemaker 1 generates a signal in response which returns to testing device 4, whereupon the return signal is analyzed by testing device 4 and results are displayed on display 8.

Test waveforms are generated by testing device 4 and applied to pacemaker 1 as follows. Where the test selected requires, for example, the transmission of atrial test waveforms to the atrial circuitry of pacemaker 1, a sequence of digital values representing the desired atrial test waveform is sent from microcomputer 7 to digital-to-analog converter 11 which produces a proportional analog voltage. This voltage is buffered and then inverted by buffer amplifier 14 and is then applied to the negative atrial terminal 23 through isolation resistor 18. Buffering here is defined to mean the use of an amplifier designed to isolate a preceding circuit from the effects of a following circuit. In a preferred embodiment of the present invention isolation resistor 18 provides a resistance of approximately 4.5K ohms.

Similarly, where ventricular test waveforms are desired, these waveforms are generated by microprocessor 7 which sends digital values to digital-to-analog converter 12, producing a proportional analog voltage which is buffered and inverted by buffer amplifier 13 which is then applied to the negative ventricular terminal 21 through isolation resistor 20. In a preferred embodiment of the present invention, isolation resistor 20 provides a resistance in the range of 4.5K ohms. One example of a digital-to-analog converter compatible with the present invention as 11 or 12, is model PMI-7528 available from Precision Monolithics, Inc. of Norwood, Mass.

Figure 3:
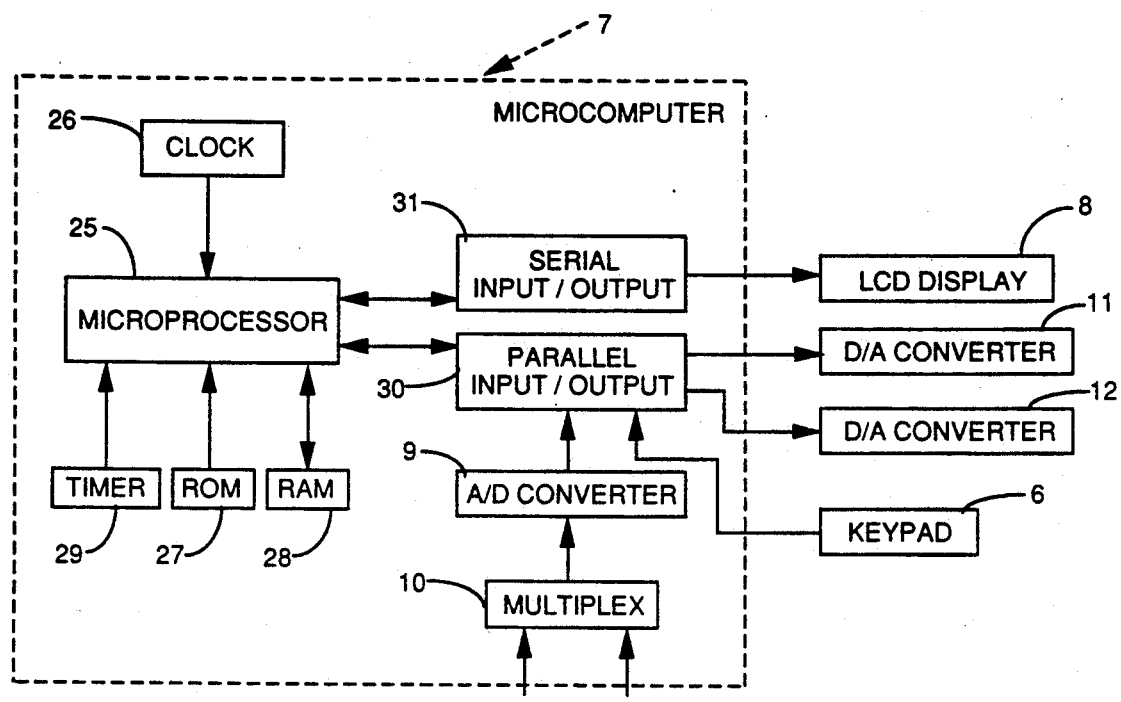
FIG. 3 is a block diagram of one embodiment of a pacemaker testing device in accordance with the present invention showing the microcomputer component of the pacemaker testing device.

Referring now to FIG. 3, the microcomputer component in accordance with one embodiment of the present invention is shown in greater detail. A highly integrated single-chip microcomputer 7, such as model 68H C11 available from Motorola, Inc. of Phoenix, Ariz., is utilized to reduce the size and power requirements of testing device 4. The microcomputer comprises microprocessor 25 which executes instructions stored in read only memory (ROM) 27. Clock 26 provides the required timing information to microprocessor 25. Microprocessor 25 monitors data entry device 6 through parallel input/output port 30 to accept input from a user of testing device 4 who is indicating which tests to perform; and to receive necessary testing parameters. These parameters are stored by microprocessor 25 in random access memory (RAM) 28, until required. Signals and voltages generated by pacemaker 1 are measured when microprocessor 25 selects the appropriate analog channel using multiplexer 10, converts the analog voltage into a proportional digital value using analog-to-digital converter 9 and then transfers the values through the parallel input/output interface 30 to system RAM 28. Test signals are generated by pacemaker testing device 4 when microprocessor 25 loads the digital values representing the desired waveform from ROM 27 and scales, (scaling being determined by an amplitude setting in RAM 28) whereupon the signals are output through parallel input/output port 30 to one of the digital-to-analog converters 11 or 12. Microprocessor 25 displays test indications and measured parameters by sending commands through serial input/output port 31 to display 8. Timing device 29 provides precise timing of external events which are detected through analog-to-digital converter 9.

Figure 4:
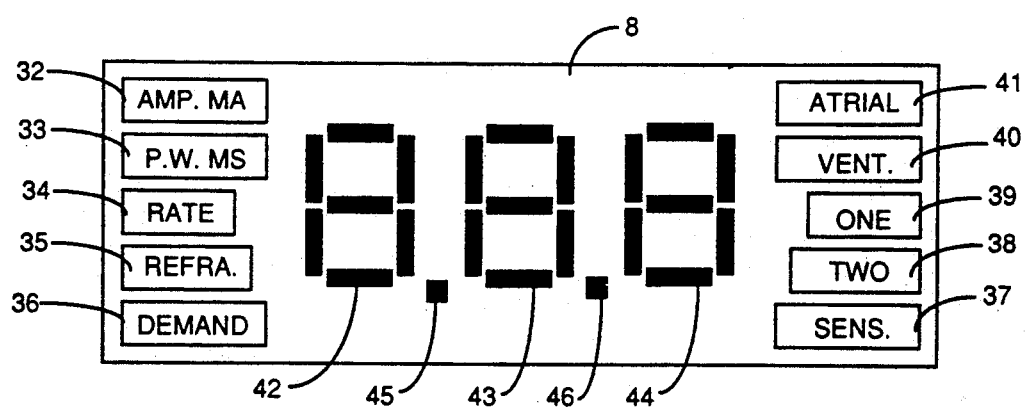
FIG. 4 is a block diagram of one embodiment of a pacemaker testing device in accordance with the present invention showing an example of a pacemaker testing device display.

FIG. 4 illustrates a preferred embodiment of a customized display 8 used in the subject invention, although it is to be understood that any display that conveys essentially the same information in a similar format is contemplated within the scope of the present invention. Display 8 includes 10 annunciators 32-41 as follows: pulse amplitude in milliamperes 32, pulse width or duration in milliseconds 33, pulse rate in beats per minute 34, refractory intervals in milliseconds 35, demand or rate compensation in beats per minute 36, sensitivity in millivolts 37, refractory interval one (stimulus refractory interval) 39, refractory interval two (sensed refractory interval) 38, a selection for a ventricular pacemaker channel 40 and a selection for an atrial pacemaker channel 41. Display 8 also includes three digits 42, 43 and 44 separated by decimal indicators 45 and 46, which are activated by microcomputer 7 as appropriate for the test selected, as explained by the foregoing discussion.

Three operations are emphasized in connection with the performance of testing device 4 and the use of those operations in performing the desired testing of pacemaker 1:

1) The first concerns the capability of testing device 4 to make measurements on and use current stimulation pulses generated by pacemaker 1 in various tests. As previously explained, current pulses generated by pacemaker 1 are first converted to proportional voltage pulses by circuitry in testing device 4. The voltage waveform is then digitized, that is, converted to a sequence of numbers created at equally spaced intervals, each proportional to the voltage at that time; this conversion is accomplished by the analog-to-digital converter 9 in testing device 4. These numbers are automatically entered into the memory of testing device 4 and are used in measuring and computing parameters associated with pulse and frequency of generation;

2) The second concerns the capability of testing device 4 to create voltage pulses that are shaped according to a sine squared function for the purpose of simulating electrical activity generated by the heart (i.e., the P wave generated by the atria and the R wave generated by the ventricles), which is then sent by testing device 4 to pacemaker 1. The sine squared function is generally suggested by pacemaker manufacturers for this purpose. Sequential values of the function are stored in the memory of testing device 4. These can be scaled to provide a pulse of a particular amplitude. The sequential numbers are provided to the input of digital-to-analog converters 11 and 12, which in turn provide a continuous analog representation of the pulse. This pulse is attenuated to an amplitude compatible with pacemaker 1, and transmitted to pacemaker 1. The duration of this pulse in the preferred embodiment is 40 milliseconds: and 3) The third concerns the capability of the testing device 4 to display parameter values with proper units. Within testing device 4 is an interface compatible with other circuitry and display 8. It is assumed that appropriate microprocessor code is written to exercise the specific features of display 8, i.e., to enunciate the correct numeric characters and associated units of measurement.

In a preferred embodiment of testing device 4, when the power is first turned on, the pacemaker initiates a self-check. The purpose of the self-check is to assure validity of the code that implements the tests performed by testing device 4. In the preferred embodiment, the procedure is to store redundant code and perform a byte-by-byte comparison to assure sameness and code integrity.

The following describes the tests performed by testing device 4. All test descriptions assume that the appropriate lead pairs for either atrial or ventricular stimulation are connected between the appropriate terminals of testing device 4 and pacemaker 1.

Binary Search Procedure

Many pacemaker tests require a means for determining interval or amplitude thresholds. To automate this threshold determination, a "binary search strategy" is employed in many of the tests which are described below.

The binary search algorithm for a search space requires one condition for implementation: that the search space be ordered such that for any test value in the search space the value to be found, hereafter referred to as the target value, must be able to be determined to be greater than, less than, or equal to said test value. This condition being met, the binary search algorithm can be described in the following steps:

1) Determine the maximum and minimum possible values that the target value can assume. These values become the current maximum and minimum search values respectively.

2) Determine the value halfway between the minimum and maximum search values: the value determined becomes the current test value.

3) Determine if the target value is greater than, less than, or equal to the test value.

4) Using the result from step 3, take one of the following actions:
   a) If the target value is equal to the test value then the target value has been determined and the search is complete.
   b) If the target value is greater than the test value then the search can be limited to only those values greater than the test value. Therefore set the new minimum search value to the value of the current test value.
   c) If the target value is less than the test value then the search can be limited to only those values less than the test value. Therefore set the new maximum search value to the value of the current test value.

5) Repeat steps 2–4 until either step 4a is reached and the exact target value is found or until the minimum and maximum search values are as close to one another as is necessary to achieve the desired precision in the approximation of the target value.

This search algorithm is very efficient. The average number of test values needed in order to determine the target value is of the order log base $2(N) = \log N/\log 2$ where N is the number of possible values that the target value can assume. For a continuous search space, N is equivalent to the size of the search space divided by the desired precision for the target value. For example, if the search space spans five volts and the desired precision is 0.1 volts, the average number of searches necessary to find the target value is log base $2(5.0/0.1) = \log$ base $2(50) = 6$.

Pulse Duration

Figure 5:
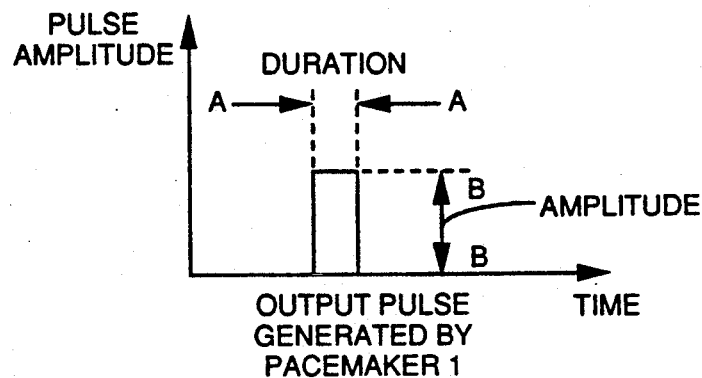
FIG. 5 is a diagrammatic illustration of a typical pacemaker pulse showing the amplitude and width/duration parameters of a pacemaker generated pulse.

PULSE DURATION OR WIDTH (for both atrial and ventricular stimulation)—referring now to FIG. 5, wherein a diagram appears showing "time" on the X axis versus "pulse amplitude" on the Y axis, and a graphic representation of a pacing pulse generated by pacemaker 1, pulse width or duration is shown by the line A—A. The pulse duration test of testing device 4 measures the width of each pacing pulse generated by pacemaker 1.

Figure 9:
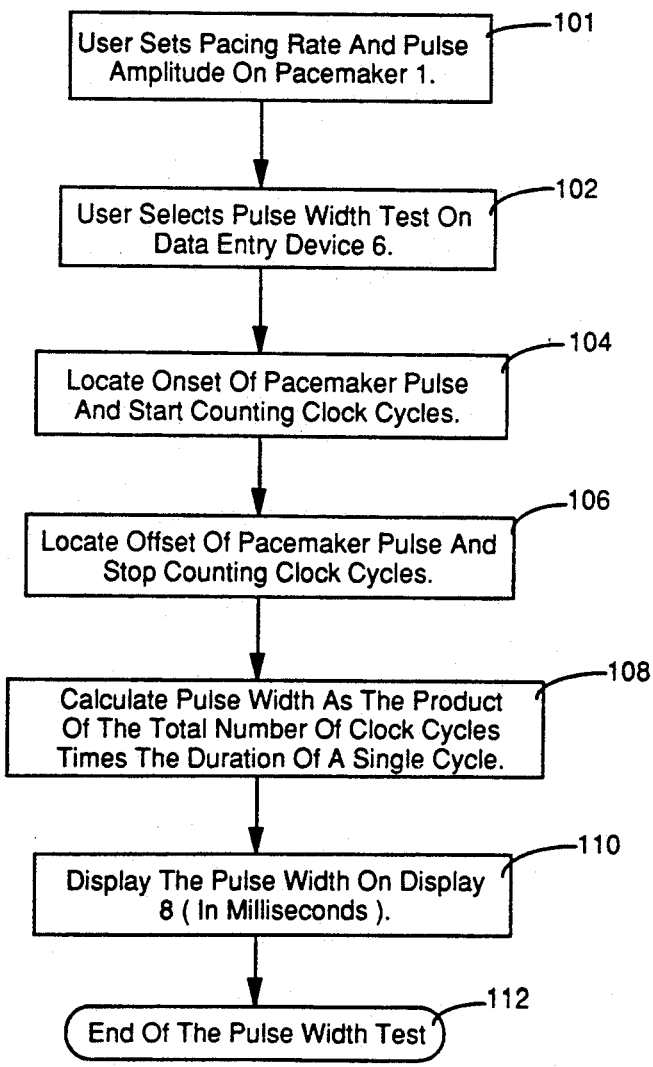
FIG. 9 is a flow diagram of one embodiment of a pacemaker testing device in accordance with the present invention showing the procedure for establishing pulse width.

Referring now to FIG. 9, there is shown a flow diagram for a computer program implementation of a portion of applicant's process of testing the pulse width. To perform this test, both pacing rate and pulse amplitude are set on pacemaker 1 in accordance with the manufacturer's instructions, step 101. The pulse duration test is selected by pressing the appropriate key on data entry device 6 as disclosed at step 102 of FIG. 9. This selection is monitored by microprocessor 25 via parallel input/output port 30 as previously described. Pacing pulses generated by pacemaker 1 are then received by testing device 4. Onset and offset of a pacing pulse generated by pacemaker 1 are determined by testing device 4 from the digitized representation of the pulse as shown in steps 104 and 106. Onset and offset of a pacing pulse generated by pacemaker 1 generally follow a rectangular wave function and are therefore well defined points. When onset is detected, the microprocessor 25 in testing device 4 begins counting internal clock cycles generated by clock 26, step 104, until offset of the pulse is determined, step 106. Pulse duration is the product of the number of clock cycles times the duration of a single clock cycle, which is calculated by microprocessor 25 as shown in step 108. Microprocessor 25 displays this value along with the proper time units by sending commands through serial input/output port 31 to display 8, as previously described and as shown in step 110. In the preferred embodiment, the time unit is milliseconds to the nearest tenth of a millisecond. In addition to displaying, results could be stored and/or printed as hardcopy if desired. This process runs continuously until the test is deselected as shown by step 112.

Common Testing Parameters and Assumptions

For the remaining test descriptions, common testing parameters which are obviously the same as those disclosed in the pulse duration test will be assumed to be the same in the remaining tests to avoid redundancy in this disclosure including, for example: the determination of onset and offset of a pulse; the transfer of data from data entry device 6 to microprocessor 25; the transfer of display commands from microprocessor 25 to display 8; the counting of clock cycles; printing and storing functions, etc.

Pulse Amplitude

PULSE AMPLITUDE (for both atrial and ventricular stimulation)—referring now to FIG. 5, wherein a diagram appears showing "time" on the X axis versus "pulse amplitude" on the Y axis and a graphic representation of a pacing pulse generated by pacemaker 1, pulse amplitude is depicted by the line B—B. The pulse amplitude test of testing device 4 measures the amplitude of each pacing pulse generated by pacemaker 1 in milliamperes.

Figure 10:
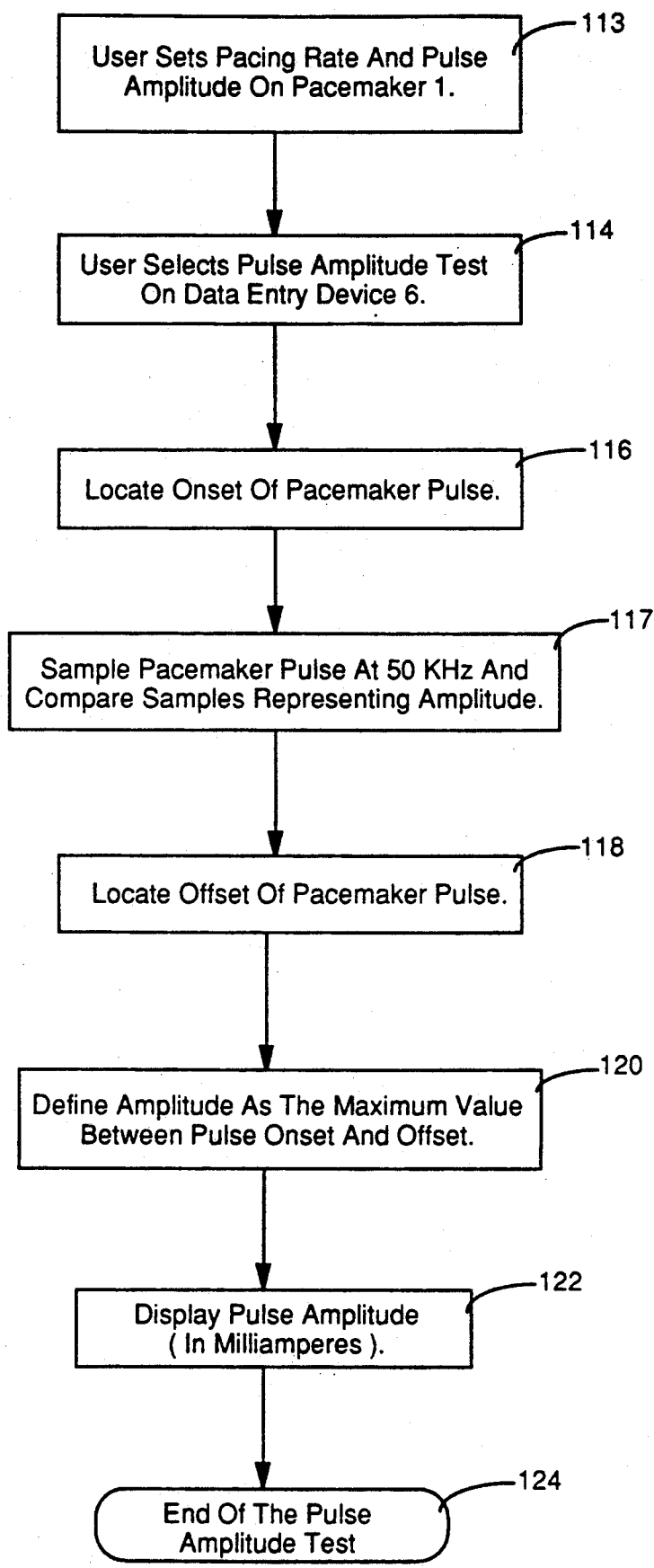
FIG. 10 is a flow diagram of one embodiment of a pacemaker testing device in accordance with the present invention showing the procedure for establishing pulse amplitude.

Referring now to FIG. 10 there is shown a flow diagram for a computer program implementation of a portion of applicant's process of testing the pulse amplitude. To perform this test, both pacing rate and pulse amplitude are set on pacemaker 1 in accordance with the manufacturer's instructions, step 113. The pulse amplitude test is selected by pressing the appropriate key on data entry device 6 as disclosed at step 114 of FIG. 10. Onset of a pacing pulse generated by pacemaker 1 is determined by testing device 4 as shown in step 116. During the interval between onset and offset, digital values representing amplitude are compared by testing device 4, step 117, at a sampling rate of approximately 50,000 samples per second until offset is determined as shown at step 118. The maximum digital value obtained during the interval is considered the amplitude of the pacing pulse generated by pacemaker 1 as shown at step 120. This digital value is proportional to the voltage of the pulse amplitude and is converted to milliamps and displayed along with the proper amplitude units as shown at step 122. In the preferred embodiment, the amplitude unit is displayed in milliamperes rounded to the nearest tenth of a milliamp. This process runs continuously until the test is deselected as shown in step 124.

Pulse Rate

Figure 6:
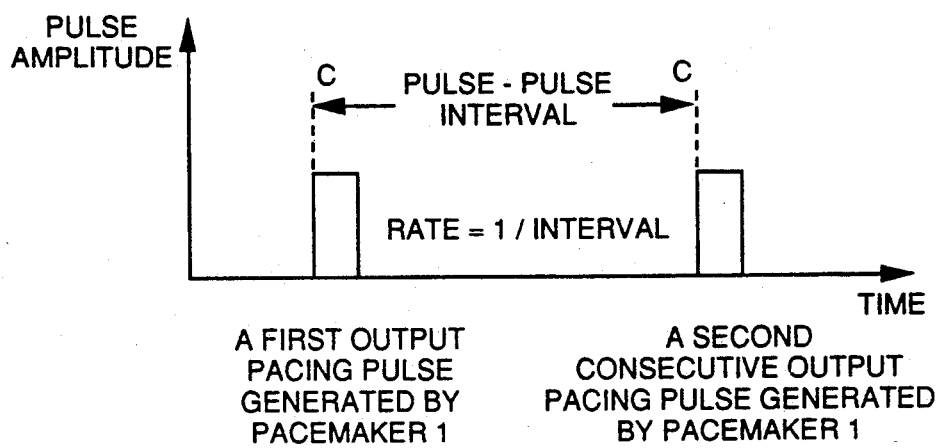
FIG. 6 is a diagrammatic illustration of the typical pulse-pulse interval between pacemaker generated pulses.

PULSE RATE (for both atrial and ventricular stimulation)—referring now to FIG. 6, wherein a diagram appears showing "time" on the X axis versus "pulse amplitude" on the Y axis, as well as a first pacing pulse generated by pacemaker 1 followed by a second consecutive pacing pulse generated by pacemaker pulse rate is depicted by the line C—C. The pulse rate test of testing device 4 measures the rate or frequency of the pacing pulses generated by pacemaker 1 per unit of time by measuring the interval between consecutive pacing pulses and calculating the mathematical reciprocal of that interval.

Figure 11:
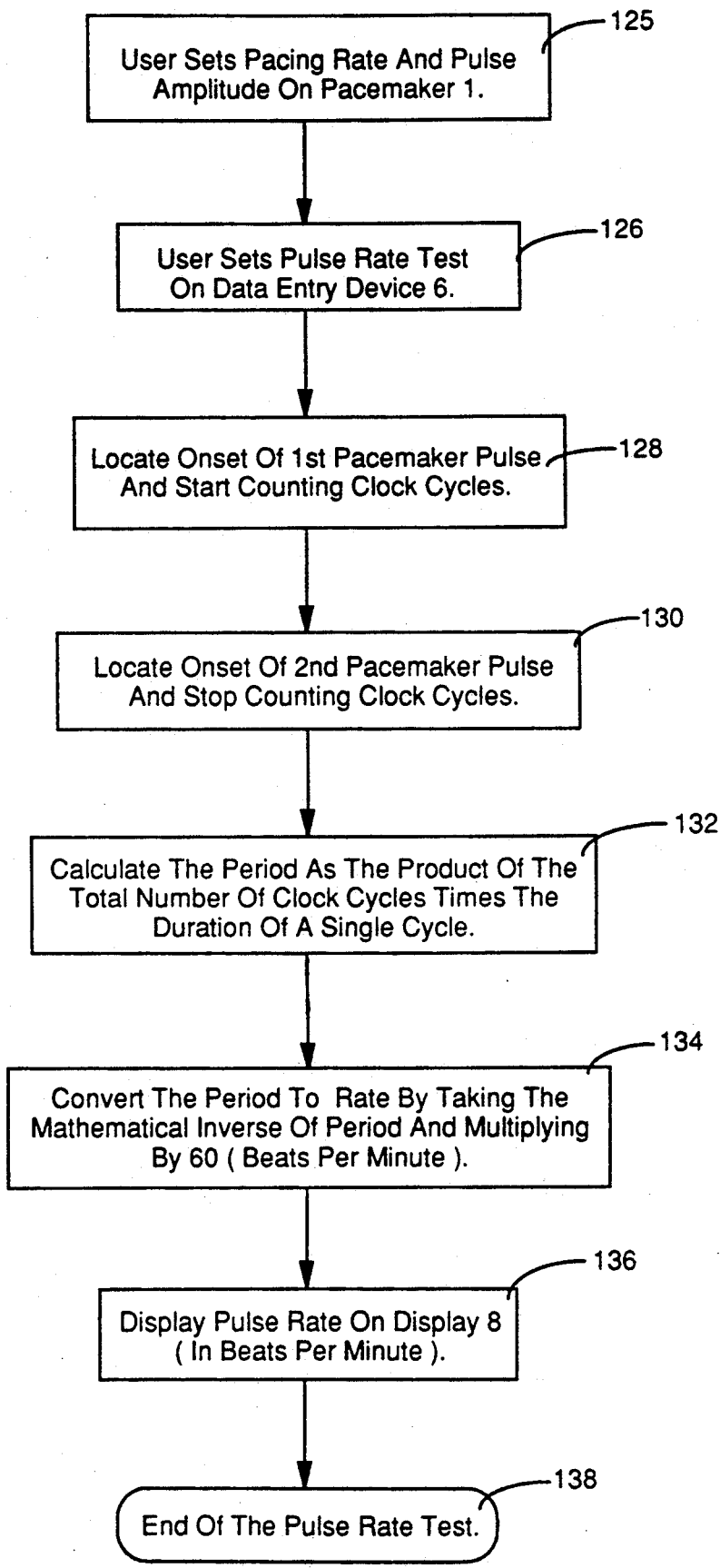
FIG. 11 is a flow diagram of one embodiment of a pacemaker testing device in accordance with the present invention showing the procedure for establishing pulse rate.

Referring now to FIG. 11 there is shown a flow diagram for a computer program implementation of a portion of applicant's process of testing the pulse rate. To perform this test, both pacing rate and pulse amplitude are set on pacemaker 1 in accordance with the manufacturer's instructions, step 125. The rate test is selected by pressing the appropriate key on data entry device 6 as disclosed at step 126 of FIG. 11. Onset of a first stimulation or pacing pulse generated by pacemaker 1 is determined as shown in step 128. When onset is detected, microprocessor 25 begins counting clock cycles until onset of a second consecutive stimulation or pacing pulse generated by pacemaker 1, as shown in step 130. The interval between pulses or "period", is computed as the product of the number of clock cycles times the duration of a single clock cycle as shown in step 132. In step 134, the mathematical reciprocal of the interval or "period" is then computed to provide the pulse rate which is then converted to beats per minute. This value is displayed as shown in step 136. This process runs continuously, in the preferred embodiment, until the test is deselected as shown in step 138.

Sensitivity

SENSITIVITY (for both atrial and ventricular stimulation)—sensitivity measures ability of pacemaker 1 to detect an electrical pulse generated by the heart. Specifically this test measures the minimum voltage amplitude that pacemaker 1 will recognize as a pulse generated by the heart.

Figure 12:
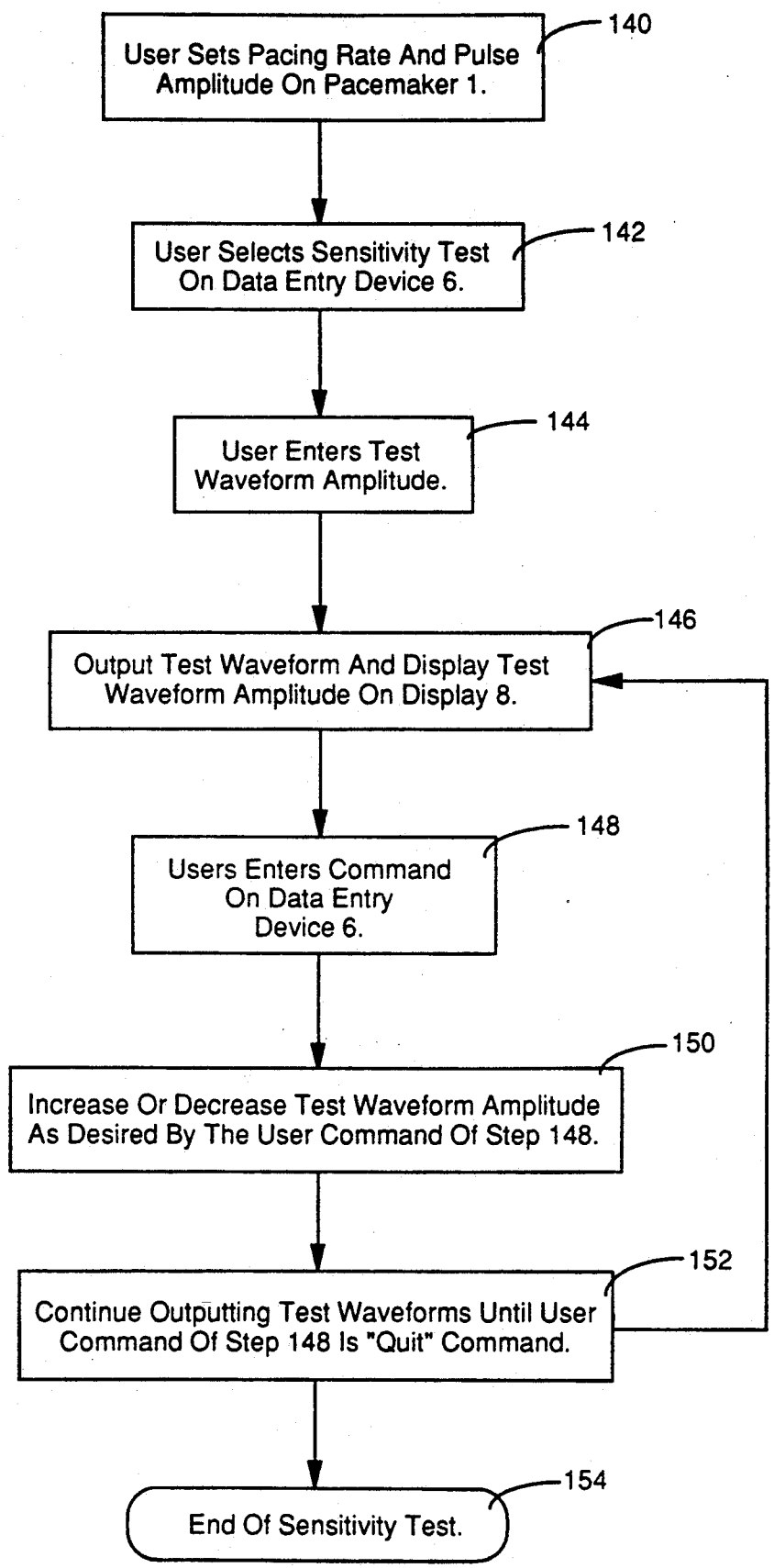
FIG. 12 is a flow diagram of one embodiment of a pacemaker testing device in accordance with the present invention showing the procedure for establishing pacemaker sensitivity.

Referring now to FIG. 12 there is shown a flow diagram for a computer program implementation of a portion of applicant's process of testing the sensitivity of pacemaker 1. To perform this test, both pacing rate and pulse amplitude are set on pacemaker 1 in accordance with the manufacturer's instructions, step 140. The sensitivity test is selected by pressing the appropriate key on data entry device 6 as disclosed in step 142 of FIG. 12. Testing device 4 then prompts the operator to enter the amplitude for the test waveform corresponding to the simulated cardiac voltage pulse to be supplied by testing device 4, shown in step 144 as corresponding to an R wave generated by the ventricle. (The following discussion of the various tests will all be discussed as generating the R wave only by way of example. It is to be noted that either the simulated R, or P, or other test waveform will be generated by testing device 4 as appropriate to the test being performed). Specifically, the amplitude is entered by the operator by pressing the appropriate keys on data entry device 6 and displayed on display 8 as shown in step 146. A test waveform of the specified amplitude is outputted to pacemaker 1 and the operator observes the "sense" indicator on pacemaker 1 for an indication that the pulse has been sensed by pacemaker 1.

The operator may vary the amplitude of the sine squared wave generated by testing device 4 as shown in step 148. In one embodiment of the present invention, the operator presses either of two designated keys, one that increases the amplitude as shown or the other that decreases the amplitude. Accordingly, the amplitude is increased or decreased as shown in step 150. The resultant amplitude is outputted to pacemaker 1 and is also shown on display 8 with the proper units, step 152. Using the manual user interactive mode, the operator continually raises and/or lowers the amplitude of the waveform until a threshold value is located for the minimum waveform which will trip or activate the "sense" indicator on pacemaker 1. Alternatively, in the preferred embodiment, this process can be automated by having testing device 4 generate an R wave the amplitude of which is continually varied pursuant to a binary search strategy until testing device 4 detects a rate compensation response (as described below) by pacemaker 1.

It has been found that in certain pacemakers, the "sense" indicator does not always accurately reflect that the pacemaker has sensed the test waveform supplied by testing device 4. Where this occurs, it has been found that the rate compensation test can be used to verify the sensitivity and the operation of the sensing indicator circuitry of such a pacemaker to ensure that the pacemaker has sensed a test waveform of a given amplitude. This verification procedure is recommended. This process runs continuously until the test is deselected as shown in step 154, in the preferred embodiment of the present invention. In the preferred embodiment of the present invention, the sensitivity is displayed in millivolts rounded to the nearest tenth of a millivolt.

Rate Compensation

Rate Compensation—(For both atrial and ventricular simulation). While pacemaker 1 can indefinitely continue to send a constant stream of equally time-spaced stimulation pulses, the spontaneous beating of the heart requires pacemaker 1 to modify its stream of pulses to avoid having pacemaker 1 send a stimulation pulse after a spontaneous heartbeat. This process is called rate or demand compensation. The rate compensation test measures the duration between a test waveform generated by testing device 4 (depicted here by way of example as a simulated R wave) and a pacing pulse generated by pacemaker 1, to ensure stimulation by pacemaker 1 at the programmed rate of the desired number of beats per minute, to compensate for the presence of the heart's own intrinsically generated beats.

Figure 13:
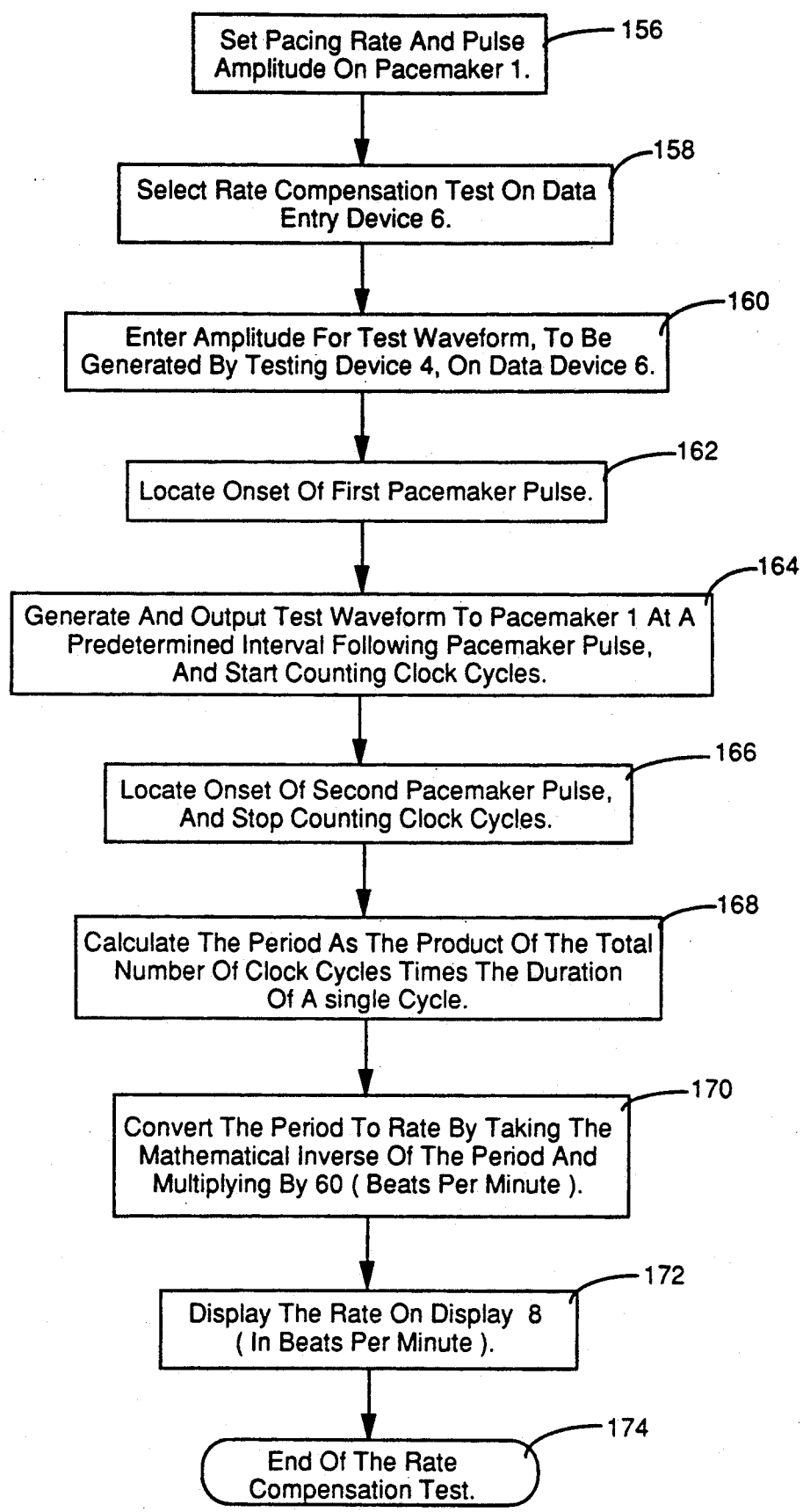
FIG. 13 is a flow diagram of one embodiment of a pacemaker testing device in accordance with the present invention showing the procedure for establishing rate compensation.

Referring now to FIG. 13, there is shown a flow diagram for a computer program implementation of a portion of applicants' process of testing the rate compensation of pacemaker 1. To perform this test, both pacing rate and pulse amplitude are set on pacemaker 1 in accordance with the manufacturer's instructions, step 156.

The rate compensation test is selected by pressing the appropriate keys on data entry device 6 as shown in step 158. The desired amplitude of test waveforms generated by testing device 4 is set by the operator by pressing the appropriate keys on data entry device 6 as shown in step 1 and must exceed the minimum amplitude that pacemaker 1 can sense. (Alternatively, testing device 4 can be designed to automatically select a testing wave of sufficient amplitude.) The onset of a first pacemaker 1 pacing pulse is located, step 162. The test waveform is transmitted to pacemaker 1 at a predetermined interval following the onset of the first pacing pulse generated by pacemaker 1 and testing device 4 begins counting clock cycles, as shown in step 164. Pacemaker 1 will interpret this test waveform as a natural heartbeat and will reset its pacing counter to 0 and restart sending pacing pulses in accordance with the pacing rate as set in step 156.

Thus, as indicated, testing device 4 locates the onset of a first pacing pulse generated by pacemaker 1, step 162, and after the lapse of a predetermined interval greater than the stimulus refractory period, but less than the interval of the mathematical inverse of the pacing rate, testing device 4 begins counting clock cycles and simultaneously generates the test waveform, step 164.

In the preferred embodiment, this predetermined interval is the refractory interval for pacemaker 1. In another embodiment, this interval could be some interval greater than the refractory interval, so long as it does not exceed the mathematical inverse of the pacing rate. Testing device 4 continues to count clock cycles until it detects the onset of a second consecutive pacing pulse generated by pacemaker 1, step 166, whereupon testing device 4 stops counting clock cycles. The "compensated" interval or period is computed as the product of the number of clock cycles times the duration of a single cycle as shown in step 168. "Compensated"

means the resetting (i.e., delay) of the pacing pulses of pacemaker 1 following a spontaneous heartbeat to conform with the presence of the heart's intrinsic spontaneous beats. The mathematical reciprocal of this period or interval is then calculated to compute the compensated pulse rate, step 170. This value is displayed, step 172. If pacemaker 1 is operating properly, the compensated rate should equal or closely approximate the pacing rate as selected in step 156. In the preferred embodiment, the rate unit is beats per minute. In the preferred embodiment, this process runs continuously until the test is deselected, step 174.

Refractory Intervals

The Refractory Intervals Test (for both atrial and ventricular stimulation) automatically measures both the "stimulus" refractory period and the "sensed" refractory period.

The "stimulus" refractory period is a short period after pacemaker 1 has generated a pacing pulse, during which pacemaker 1 is temporarily "blinded" or "numbed" and is unable to sense any electrical artifacts, regardless of source. This "blind" period is intentionally designed into pacemaker 1 so that pacemaker 1 does not sense its own pacing pulse or the R wave that is generated by the heart in response to the pacing pulse and mistake that pulse for a spontaneous pulse generated by the heart. Specifically, the stimulus refractory period begins immediately after pacemaker 1 has generated a pacing pulse and ends at that point in time when pacemaker 1 is again able to sense pulses from whatever source.

A similar "blind" or "numb" period occurs immediately after pacemaker has sensed a waveform, from whatever source. Thus, the "sensed" refractory period is the minimum interval or period of time after pacemaker 1 has sensed a waveform, that pacemaker 1 can again sense another waveform. Specifically this period begins immediately after pacemaker 1 has sensed a waveform and ends at that point in time when pacemaker 1 is again able to sense waveforms. Both the "stimulus" and "sensed" refractory periods are diagrammatically shown in FIG. 8. The rectangular waveforms in FIG. 8 correspond to pacing waveforms generated by pacemaker 1. The bell-shaped waveforms correspond to waveforms sensed by pacemaker 1. These sensed waveforms can be either those waveforms generated naturally by the heart, or these waveforms can be test waveform patterns generated by testing device 4. When performing the "sensed" refractory intervals test, these bell-shaped waveforms are generated by testing device 4.

Measurement of the Stimulus Refractory Period

Figure 8:
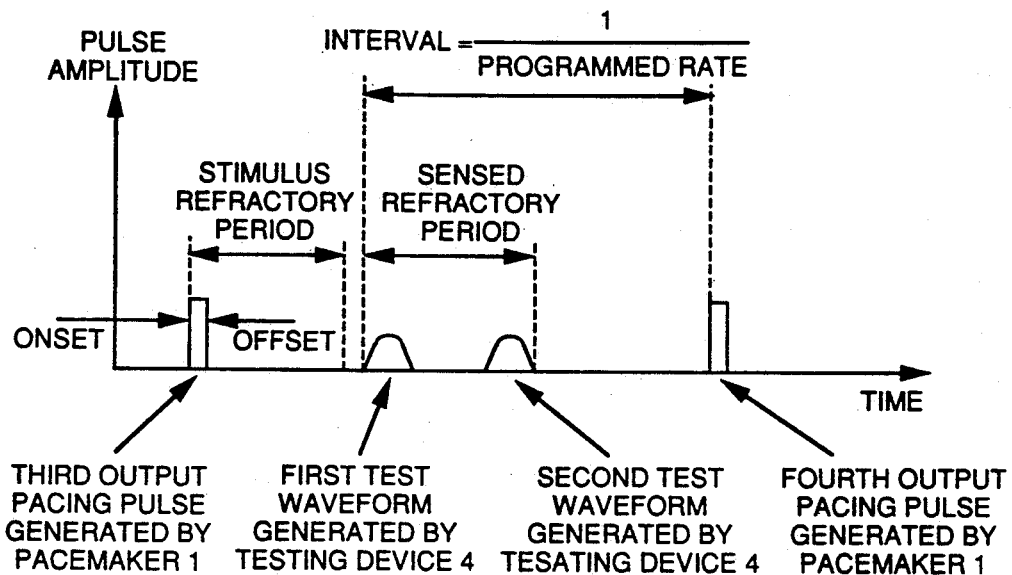
FIG. 8 is a diagrammatic illustration of the measurement of refractory intervals of a typical pacemaker.
Figure 14:
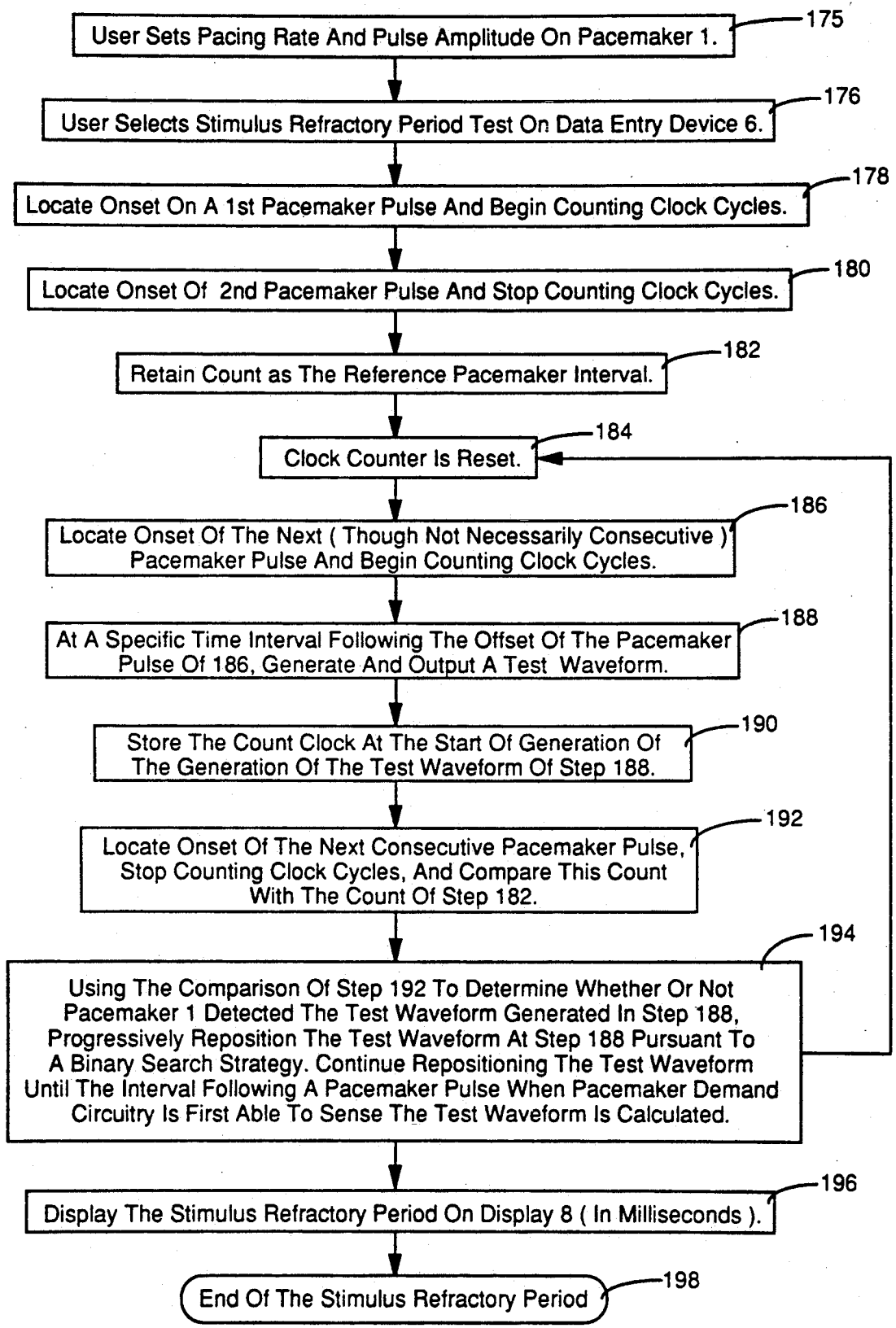
FIG. 14 is a flow diagram of one embodiment of a pacemaker testing device in accordance with the present invention showing the procedure for establishing a stimulus refractory interval.

In FIG. 8 there is shown a graphic representation of the determination of both the stimulus refractory period and the sensed refractory period. FIG. 14 shows a flow diagram for a computer program implementation of a portion of the process of testing stimulus refractory intervals.

Referring now to FIGS. 8 and 14, measurement of the first or stimulus refractory period or interval proceeds as follows.

Both pacing rate and pulse amplitude are selected on pacemaker 1 in accordance with the manufacturer's instructions, step 175. It is imperative that the pacing rate not be changed during the test.

The first or stimulus refractory interval test is selected by pressing the appropriate keys on data entry device 6, step 176.

Onset of a first pacing pulse generated by pacemaker 1 is located by testing device 4, and testing device 4 begins counting cycles, step 178.

Testing device 4 continues counting cycles until the onset of a second consecutive pacing pulse generated by pacemaker 1 is located by testing device 4, step 180.

In step 182, testing device 4 retains the count obtained at the onset of the second consecutive pacing pulse. This count provides a verification by testing device 4 of the interval or period between pacing pulses generated by pacemaker 1, as set by the operator in step 175, and is essentially the same as the pulse rate test as described earlier.

The clock counter of testing device 4 is now reset to start a fresh count, step 184.

Testing device 4 now locates the onset and offset of a third (though not necessarily consecutive) pacing pulse generated by pacemaker 1 and again begins counting clock cycles, step 186.

In step 188, because testing device 4 does not yet know at what point the stimulus refractory period of pacemaker will end, testing device 4 selects a point in time equal to half of the pacing interval after the offset of this third pacing pulse pursuant to a binary search strategy, and generates a first test waveform which will be sent to pacemaker 1. Testing device 4 does not know if this test waveform will be received by pacemaker 1 during ("inside") or after ("outside of") of pacemaker 1's stimulus refractory period. In any event, the amplitude of this test waveform must exceed the minimum sensitivity of pacemaker 1 to ensure that pacemaker will be able to sense the test waveform, if in fact the test waveform is sent to pacemaker 1 outside of the refractory period of pacemaker 1.

The clock count at the start of the generation of this first test waveform is stored, step 190.

In step 192, testing device 4 continues counting clock cycles until it detects the onset of a fourth consecutive pacing pulse generated by pacemaker 1 and testing device 4 compares this count with the count of step 182.

If the first test waveform generated by testing device 4 was not sensed by pacemaker 1, the test waveform will obviously not have had any effect on the pacing rate of pacemaker 1 as determined in step 182. Therefore, if the count of step 192 equals the count of step 182, the test waveform was sent to pacemaker 1 during the stimulus refractory period of pacemaker 1.

If, on the other hand, the count of step 192 is larger than the count of step 182, the first test waveform has occurred outside of the stimulus refractory period of pacemaker 1 and was sensed by pacemaker 1. Clearly, pacemaker 1 reinitialized its pacing count which determines when it will generate the next pacing pulse and restarted its pacing count beginning with its reception of the test waveform, thus delaying the generation of the fourth pacing pulse from pacemaker 1 in step 192, vis-a-vis step 182, resulting in a longer count by pacemaker tester 4.

Whatever the result, whether the first test waveform was sensed by pacemaker 1 or not, testing device 4 continues the binary search process (to determine that minimum interval after a pacing pulse that the test waveform is first sensed by pacemaker 1).

As shown in step 194, specifically, if the first test waveform was detected, testing device 4 will decrease the time interval that was utilized between the sensed onset of the third pacing pulse and the generation of the test waveform to attempt to generate a test waveform during the stimulus refractory interval following a subsequent pacing pulse. Alternatively, if the first test waveform was not detected, testing device 4 will increase the time interval that was utilized between the sensed onset of the third pacing pulse and the generation of the test waveform to attempt to generate a test waveform outside the stimulus refractory interval following a subsequent pacing pulse. Thus, in step 194, testing device 4 continues to sequence through the processes of detecting onset of a pacing pulse generated by pacemaker 1 and initiating a count of clock cycles, generating a test waveform at a computed interval after the pacing pulse based on whether the previous test waveform was detected so that the delay interval is alternately lengthened or shortened as this process is done after subsequent pacing pulses, detecting the onset of the next occurring pacing pulse generated by pacemaker 1, and comparing the clock count obtained representative of the interval between pacing pulses to that obtained in step 182. This sequence of processes is performed a sufficient number of times to locate the minimum interval after a pacing pulse that a test waveform is sensed by pacemaker 1.

In another and preferred embodiment of the present invention the process of step 194 is subject to verification, by which it is meant that the process of step 194 is repeated several times for each computed interval, in effect repeating wave generation with several test waveforms for each interval. The results of each wave generation at a single interval are compared and microprocessor 25 does not accept those results until the same result appears with a sufficient frequency to verify its validity. The number of wave generations at a single interval and the frequency may be varied as desired, but in the preferred embodiment of the present invention the results are not considered verified until 3 out of 5 results are the same. The sensed refractory period, discussed below, is also subject to this verification procedure in the preferred embodiment of the present invention.

The length of the stimulus refractory interval or period is displayed on display 8, along with the proper time units, step 196. In the preferred embodiment, the time unit is milliseconds, rounded to the nearest millisecond.

In the preferred embodiment, this test continues to display the test result until it is deselected, step 198.

Measurement of the Sensed Refractory Period

Figure 15:
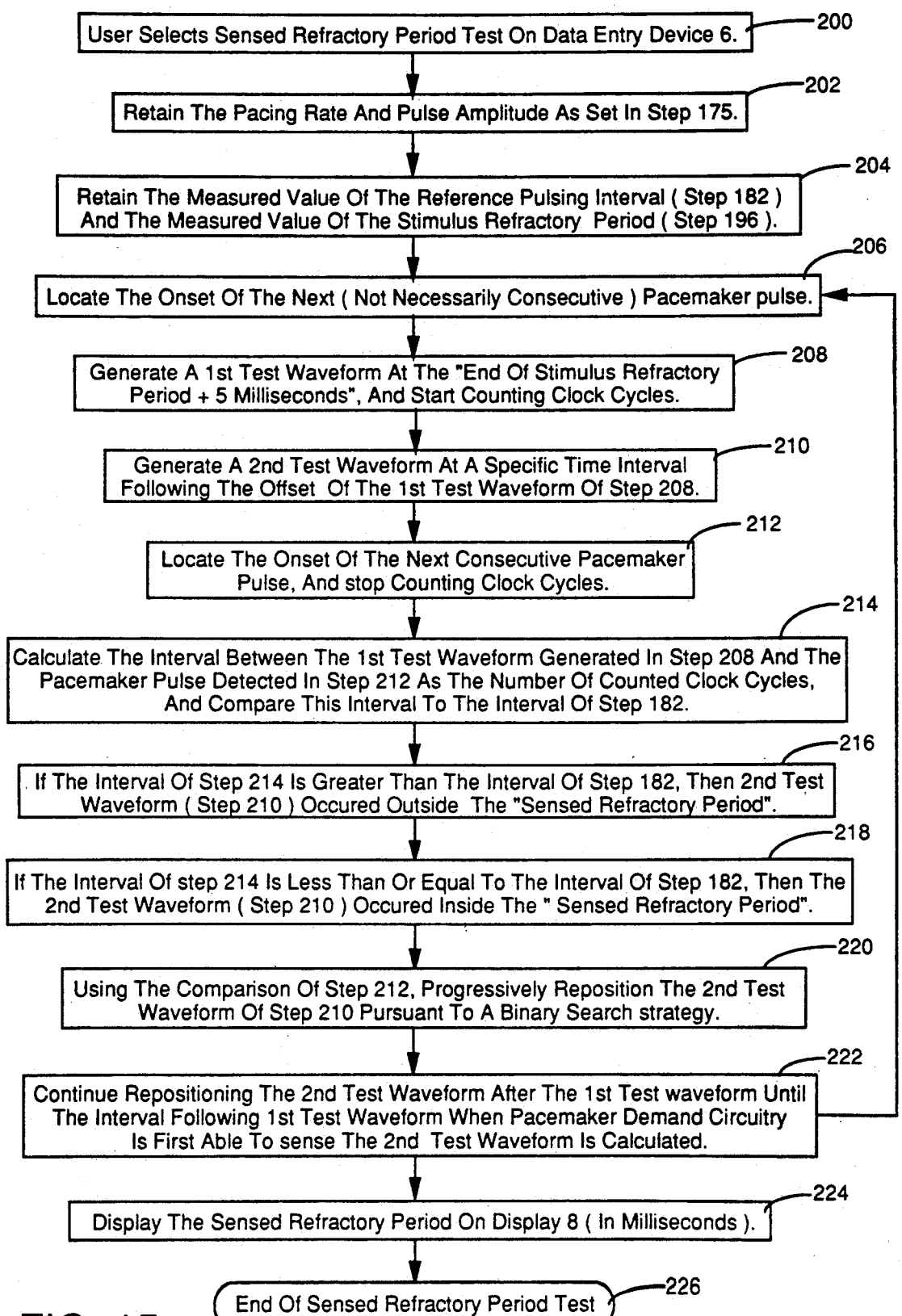
FIG. 15 is a flow diagram of one embodiment of a pacemaker testing device in accordance with the present invention showing the procedure for establishing a sensed refractory interval.

Measurement of the sensed refractory period is as follows. Referring now to FIG. 8, previously described, and FIG. 15, which shows a flow diagram for a computer program implementation of a portion of the process of testing sensed refractory intervals, in step 200, the sensed refractory period test is selected by pressing the appropriate keys on data entry device 6.

In step 202, pacing rate and pulse amplitude as set in step 175 are either retained or reentered into pacemaker 1.

As shown in step 204, testing device 4 either retains the measured values for both the interval between programmed pacing pulses (step 182) and also the stimulus refractory period (step 196), or determines those values in accordance with the process as outlined above.

Testing device 4 locates the onset of a first pacing pulse generated by pacemaker 1, step 206.

As shown in step 208, following onset of said first pacing pulse, testing device 4 then adds a set amount of time to the stimulus refractory period value before generating a first test waveform for the sensed refractory period test. (Although the test waveform can be any waveform, it is depicted by way of example in FIG. 8 as an R waveform.) In the preferred embodiment, this set amount of time is 5 milliseconds. Testing device 4 begins counting clock cycles from the point of generation of said first test waveform.

Having determined the stimulus refractory period (step 196), two facts become evident when testing device 4 generates a single test waveform at "end of stimulus refractory period + 5 milliseconds." First, this test waveform will be outputted to pacemaker 1 outside of its stimulus refractory period and therefore must certainly be sensed by pacemaker 1. Second, the interval from onset of the single test waveform to the next pacing pulse must equal the interval determined and saved in step 182.

Testing device 4 generates a first test waveform at "end of refractory period + 5 milliseconds" as shown in step 208 followed by a second test waveform (depicted by way of example in FIGS. 8 and 15 as an R wave) generated at a set interval from the offset of the first test waveform.

If the second test waveform is detected by pacemaker 1, the time interval from onset of the first test waveform to the next pacing pulse will be larger than the value of the interval saved in step 182 because the pacemaker will reinitialize its pacing count and restart its count with the sensed second test waveform.

If the second test waveform is not detected by pacemaker 1, the interval from onset of the first test waveform to the next pacing pulse will remain unchanged, i.e., will be equal in value to the interval saved in step 182.

Thus, in step 212, testing device 4 locates the onset of the second consecutive pacing pulse generated by pacemaker 1 after step 206.

Testing device 4 then calculates the interval between the first test waveform generated in step 208 and the second pacing pulse detected in step 212 as the number of counted clock cycles, and compares this interval to that interval of step 182.

As shown in step 216, if the interval between the first test waveform and the second pacing pulse of step 214 is greater than the interval of step 182, the second test waveform occurred outside the sensed refractory period of pacemaker 1 and therefore was sensed by pacemaker 1 causing the pacemaker 1 count to reset its pacing count.

As shown in step 218, if the interval between the first test waveform and the second pacing pulse is less than or equal to the interval of step 182, then the second test waveform of step 210 occurred inside the sensed refractory period of pacemaker 1 and therefore was not sensed by pacemaker 1.

In step 220, it is shown that if the second test waveform was detected by pacemaker 1, then the interval between generation of the first test waveform and the second test waveform is decreased according to a binary search strategy in an effort to cause the second test waveform not to be detected by pacemaker On the other hand, if the second test waveform was not detected by pacemaker 1, then the interval between the generation of the first test waveform and the second test waveform is increased according to a binary search strategy in an effort to cause the second test waveform to be detected by pacemaker 1.

In step 222, it is shown that the sequence of steps to locate the onset of a subsequent pacing pulse, to generate a first test waveform after the pacing pulse at the "end of stimulus refractory period +5 milliseconds," to generate a second test waveform whose delay interval after the first test waveform is governed by whether the previous second test waveform was sensed or not with repositioning pursuant to a binary search strategy, to locate onset of the next subsequent pacing pulse, to determine if the second test waveform was detected (steps 206 to 220) are performed a sufficient number of times to locate the minimum interval after a first test waveform that a second test waveform is detected by pacemaker 1. This interval is the sensed refractory interval and is displayed along with the proper time units in step 224. In the preferred embodiment of the present invention, the time unit is milliseconds rounded to the nearest millisecond.

In the preferred embodiment, this process continues to display the test result until the test is deselected, step 226.

A-V Delay

Figure 7:
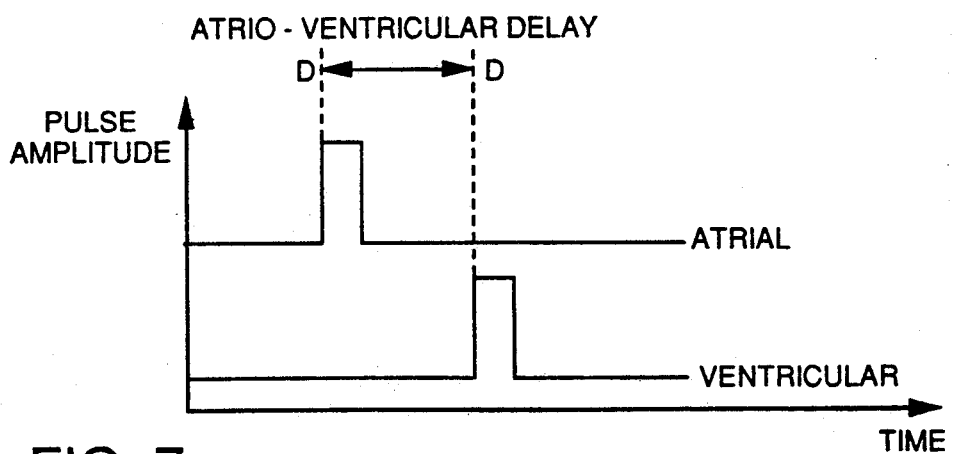
FIG. 7 is a diagrammatic illustration of the atrio-ventricular delay interval of a typical pacemaker.

A-V delay measures the delay between the onset of the atrial pacing pulse and the ventricular pacing pulse. This is shown graphically in FIG. 7 wherein the X axis is time; the Y axis is pulse amplitude; and a first atrial pacing pulse is shown followed by a second ventricular pacing pulse, both pulses being generated by pacemaker 1. The line D—D is the atrio-ventricular delay.

Figure 16:
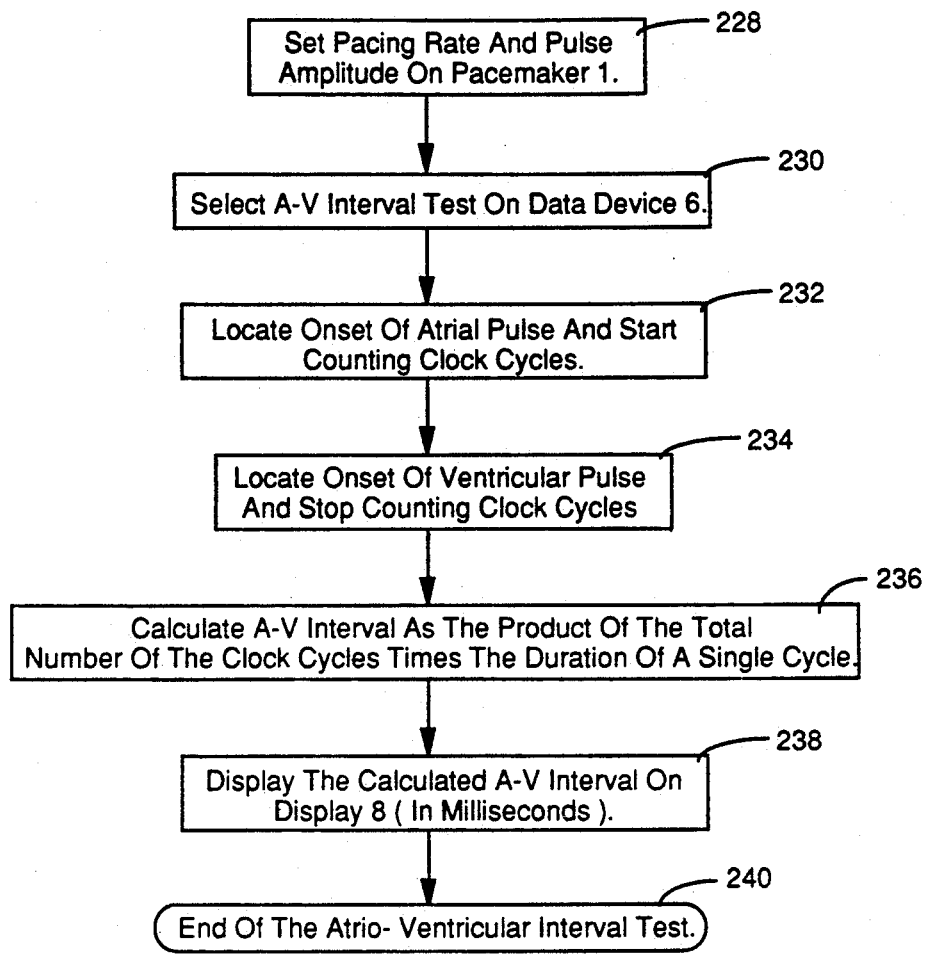
FIG. 16 is a flow diagram of one embodiment of a pacemaker testing device in accordance with the present invention showing the procedure for establishing atrio-ventricular delay.

Referring now to FIG. 16, both pacing rate and pulse amplitude are set on pacemaker 1, step 228. The A-V test interval is selected by pressing the appropriate key on data entry device 6 as shown in step 230 in FIG. 15. The onset of the atrial pacing pulse is detected by testing device 4, step 232. At this time, it begins counting internal clock cycles. It continues to count cycles until it detects the onset of the ventricular pacing pulse, step 234. The A-V Delay is the product of the number of clock cycles times the duration of a single clock cycle, step 236. This value is displayed along with proper time units, step 238. In the preferred embodiment of the present invention, the time unit is milliseconds rounded to the nearest millisecond. In the preferred embodiment this process runs until the test is deselected, step 240.

Direct Current Leakage Test

Figure 17:
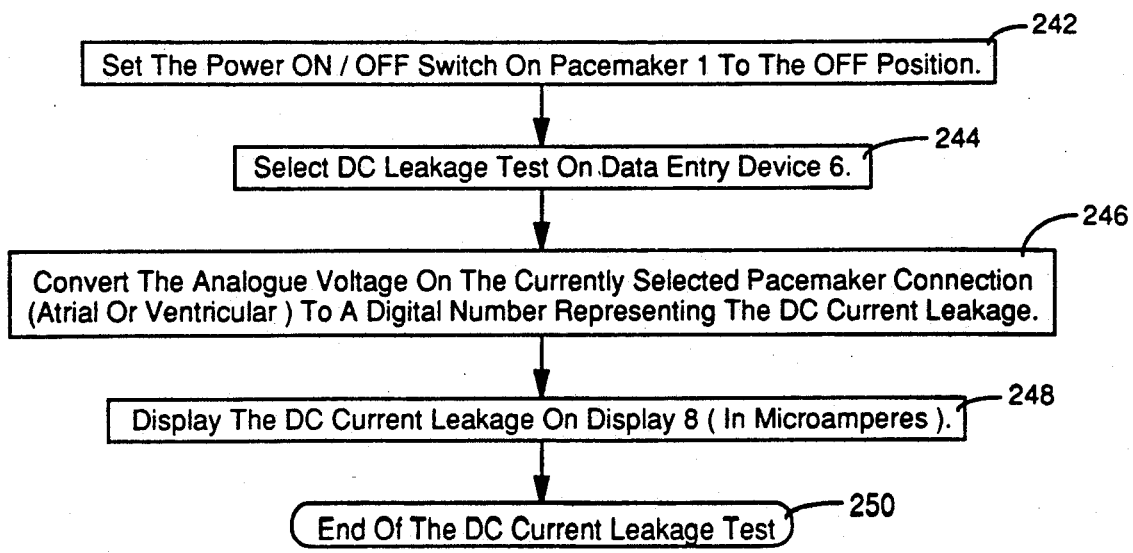
FIG. 17 is a flow diagram of one embodiment of a pacemaker testing device in accordance with the present invention showing the procedure for establishing direct current leakage.

Referring now to FIG. 17, a flow diagram for a computer program implementation comprises even-numbered steps 242-250 of a portion of the process of testing D.C. leakage.

The direct current (DC) leakage test measures the amount of current which flows between the positive and negative ventricular output terminals of pacing device 4 when the pacemaker power ON/OFF switch is set to OFF. This leakage current appears as a voltage across load resistor 19. The voltage measures should not exceed 5 millivolts, indicating a peakage current of 10 microamperes. For A-V sequential pacemakers, the leakages test is repeated to measure the current flowing between the positive and negative atrial output terminals of pacing device 4 when the pacemaker power ON/OFF switch is set to OFF. This leakage current appears as a voltage across load resistor 17, and is amplified and converted to digital value. The result is displayed in microamperes rounded to the nearest tenth of a microampere.

A.C. Interference Test

Figure 18:
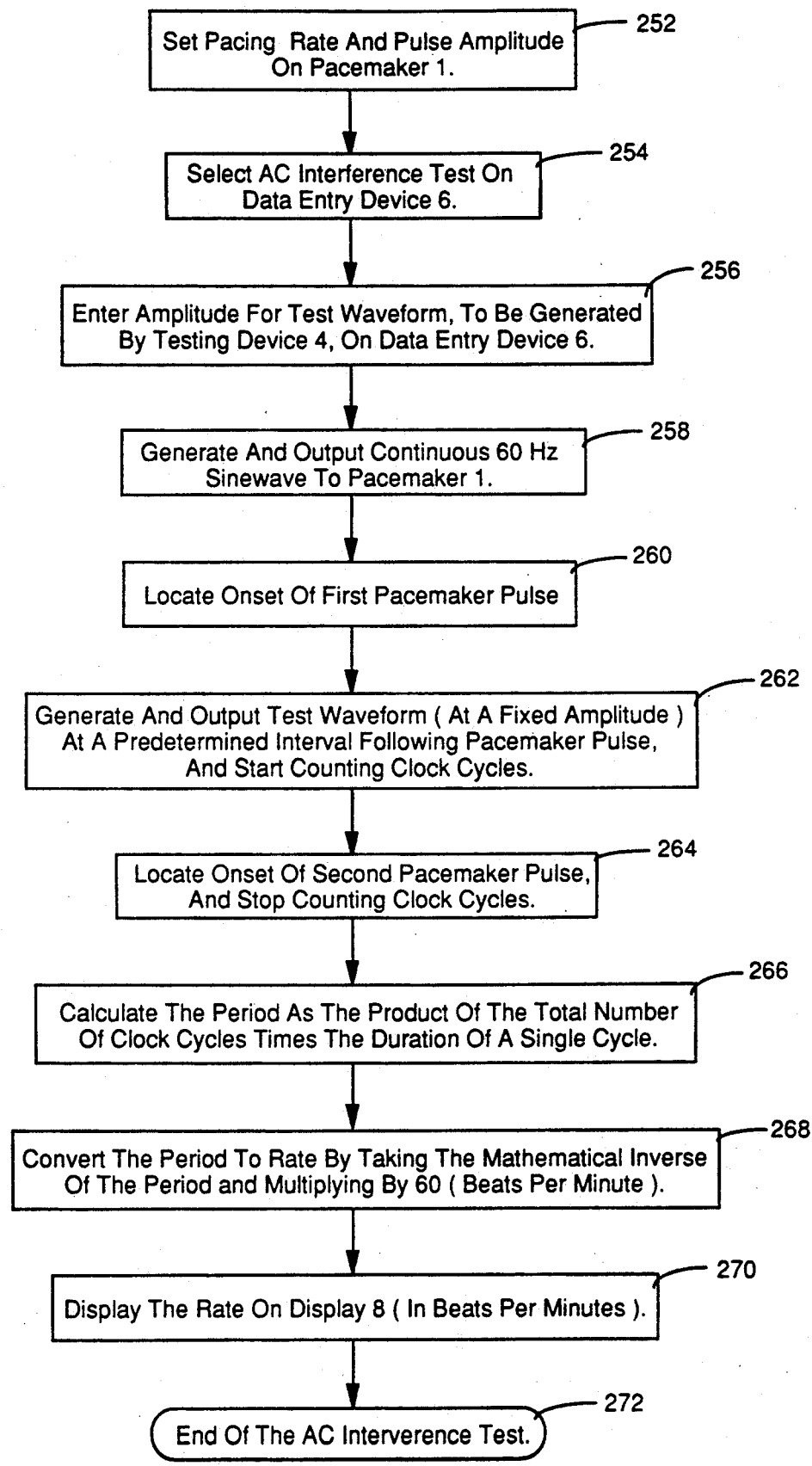
FIG. 18 is a flow diagram of one embodiment of a pacemaker testing device in accordance with the present invention showing the procedure for establishing A.C. interference.

Referring now to FIG. 18, a flow diagram for a computer program implementation comprises even-numbered steps 252-272 of a portion of the process for testing A.C. interference.

The A.C. interference test is performed to ensure that the pacemaker is not overly sensitive to 60 Hz A.C. power line interference. The pacemaker sense circuitry should suppress A.C. interference and still be able to detect R waves.

The test is performed by outputting a test waveform at a fixed rate (120 BPM) while simultaneously outputting a 60 HZ sine wave simulating A.C. interference. The pacemaker 1 should correctly sense the test waveforms which are verified by observing the pacemaker sense indicator. Alternatively, the test can be performed automatically by monitoring the pacemaker pulse-to-pulse interval to detect changes indicating that the test waveform was correctly sensed to determine the maximum sine wave amplitude which can be tolerated before erroneous sensing occurs. The resulting measurement is displayed in units of millivolts rounded to the nearest tenth of a millivolt.

Frequency Response Test

Figure 19:
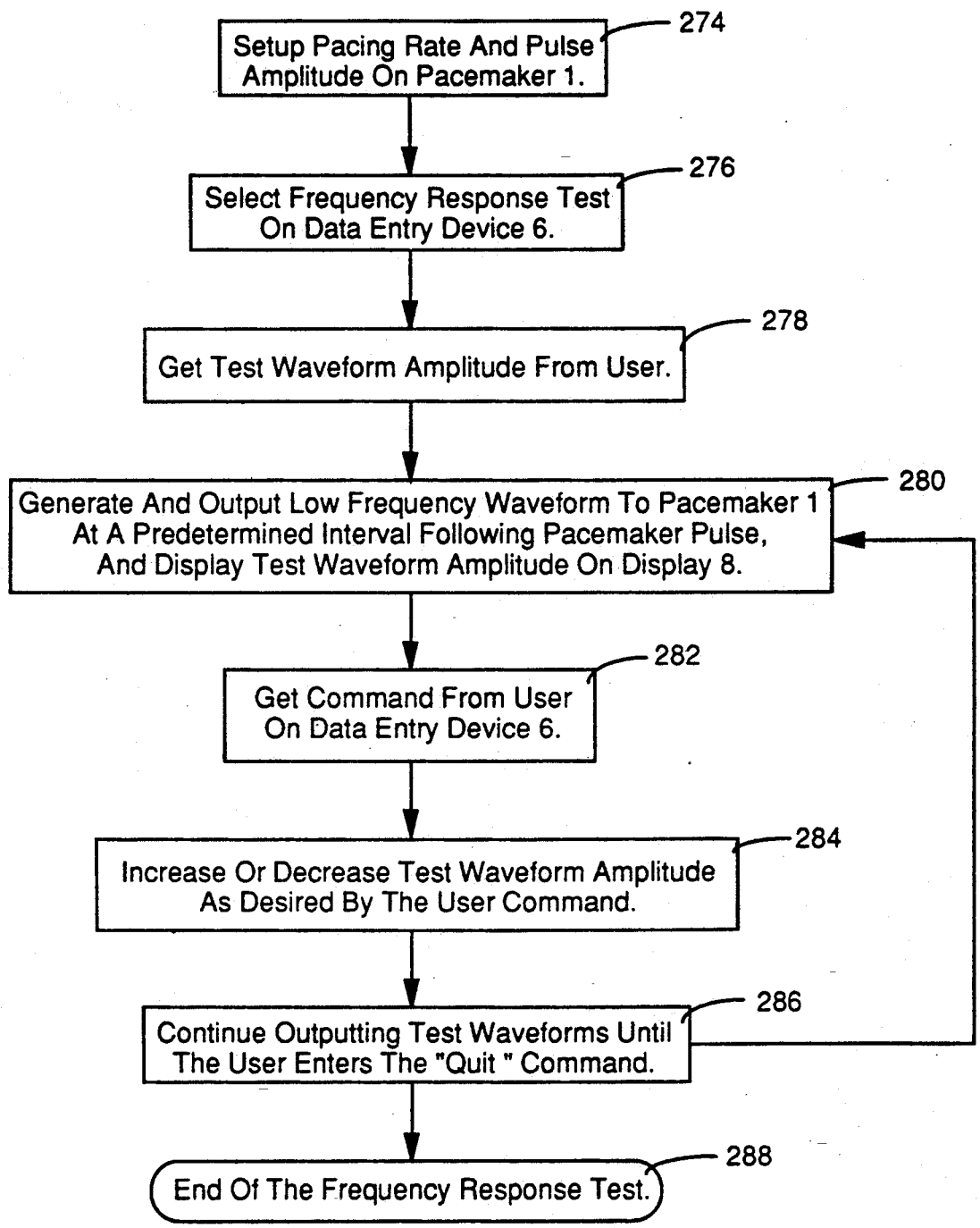
FIG. 19 is a flow diagram of one embodiment of a pacemaker testing device in accordance with the present invention showing the procedure for establishing frequency response.

Referring now to FIG. 19, a flow diagram for a computer program implementation comprises even-numbered steps 274-288 of a portion of the process for testing frequency response.

The frequency response test is performed to ensure that the pacemaker sense circuitry adequately attenuates waveforms outside the primary QRS complex frequency range. The pacemaker sense circuitry is designed to avoid triggering from lower frequency waveforms such as P waves and T waves as well as from higher frequency waves.

The test is performed by setting the pacemaker sensitivity control to maximum sensitivity and the pacemaker rate to 120 beats per minute. A 200 millisecond sine squared pulse (5 Hz) is generated at increasing amplitudes until sensed by the pacemaker as determined by the sense indicator. This value is displayed as the low-frequency sensitivity (should be 9 millivolts or greater). Next, a 1 millisecond sine squared pulse (1000 Hz) is generated at increasing amplitudes until sensed by the pacemaker as determine by the sense indicator. This value is displayed as the high-frequency sensitivity (should be 5 millivolts or greater) in units of millivolts rounded to the nearest tenth of a millivolt.

Battery Current Drain Test

Figure 20:
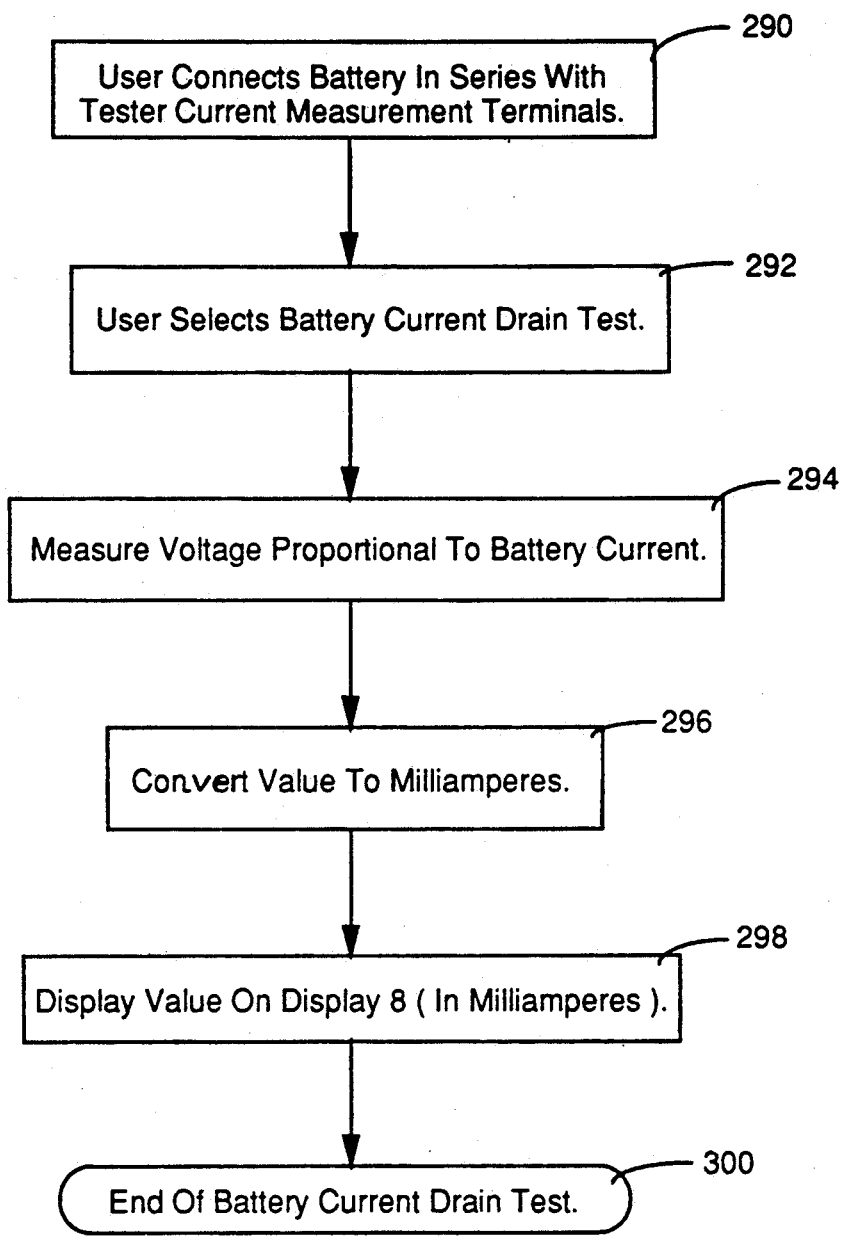
FIG. 20 is a flow diagram of one embodiment of a pacemaker testing device in accordance with the present invention showing the procedure to establish battery drain.

Referring now to FIG. 20, a flow diagram for a computer program implementation comprises even-numbered steps 290-300 of a portion of the process for testing battery current drain.

The battery current drain test is performed to check the amount of current drawn by the pacemaker at specified operating conditions and while the pacemaker is turned off. The pacemaker battery is removed and reconnected such that testing device terminals 58 and 60 are in series with the negative battery terminal connection. The testing device measures the battery current drain and displays the result to the nearest tenth of a milliampere.

Having described the present invention in detail, its many advantages become obvious. The present invention is truly portable, comprising a totally hand held unit. When powered by a battery source, testing device 4 is completely portable. Its lightweight and portability, coupled with its ability to perform a fully comprehensive testing of medical pacing units, permits full testing of medical pacer units outside of the laboratory setting. Because the unit is self-contained, no additional testing equipment such as oscilloscopes, multimeters or additional computers are required to perform comprehensive testing.

The present invention also significantly reduces the time necessary to perform comprehensive testing. In the laboratory setting, comprehensive testing typically required one and one-half hours per medical pacing unit. With the present invention, testing time is reduced to approximately 10-15 minutes per medical pacing unit to perform the full battery of tests. This time savings is realized in part because of the pre-programmed nature of present invention; a reduction in set up time; the use of binary search strategy to expedite obtaining testing results; and because the portability of testing device 4 eliminates the time necessary to transport medical pacing units back to the laboratory setting for comprehensive testing.

Finally, the present invention provides for more accurate testing results via the use of an internal verification procedure.

Having described the invention in detail and by reference to preferred embodiments thereof, it will be apparent that modifications and variations are possible without departing from the scope of the invention defined in the appended claims.

What is claimed is:

1. A self-contained, portable medical pacing unit tester capable of quickly and comprehensively testing medical pacing units comprising:
   (a) a means for transferring signals between said tester and said pacing unit which is being tested by said tester;
   (b) a data entry device, said data entry device further comprising a means to select at least one medical pacing unit test and to input one or more medical pacing unit parameters where said parameters are necessary to perform said selected medical pacing unit test;
   (c) a means for timing intervals associated with performing said pacing unit test;
   (d) a means to generate a set of test signals to be sent to said pacing unit when required for said medical pacing unit test, said means for generating said set of test signals further comprising a microcomputer and a digital/analog converter wherein said microprocessor further comprises a means for generating a series of digital values corresponding to at least one analog test waveform appropriate for said selected medical pacing unit test and a means for transferring said digital values to said digital-/analog converter, said digital/analog converter further including a means for generating at least one corresponding analog test waveform and a means for transferring said analog test waveform to said pacing unit;
   (e) a means to analyze a set of pacing signals received by said tester from said pacing unit, wherein said set of pacing signals generated by said pacing unit comprises at least one analog waveform whereupon said means for analyzing further comprises an analog/digital converter for converting said analog waveform to a series of digital values corresponding to said analog waveform, and a microcomputer for analyzing said digital values with programming appropriate to said selected medical pacing unit test; and
   (f) a means to display result(s) of said analysis;
   (g) wherein said means to select said medical pacing unit test includes a means to select a stimulus refractory interval test wherein said means to select said stimulus refractory interval test further includes:
   (1) a means to generate at least one test waveform and transmit said test waveform to said pacing unit;
   (2) a means to determine an interval between successive of said pacing signals generated by said pacing unit, wherein each of said pacing signals initially form an analog waveform of a pacing pulse which is converted to proportional digital values by said tester;
   (3) a means to control voltage amplitude of said test waveform;
   (4) a means to position said test waveform at a specific interval after the generation of one of said one or more pacing signals generated by said pacing unit;
   (5) a means to measure an interval between successive pacing signals generated by said pacing unit, said interval now containing said test waveform of step (4) generated by said tester;
   (6) a means to compare said interval of step (5) with said interval of step (2) to determine whether or not said positioned test waveform was detected by said pacing unit, said detection by said pacing unit being indicated by an increase of said interval of step (5) over said interval of step (2);
   (7) a means to repeat steps (4)-(6), continually repositioning said test waveform pursuant to a binary search strategy to calculate an interval after generation of said pacing signals generated by said pacing units when demand circuitry of said pacing unit is first able to sense said test waveform.

2. The tester as defined in claim 1, further including a means to repeat said steps (4)-(6) for each positioning of said positioned test waveform to very the results obtained.

3. A self-contained, portable medical pacing unit tester capable of quickly and comprehensively testing medical pacing units comprising:
   (a) a means for transferring signals between said tester and said pacing unit which is being tested by said tester;
   (b) a data entry device, said data entry device further comprising a means to select at least one medical pacing unit test and to input one or more medical pacing unit parameters where said parameters are necessary to perform said selected medical pacing unit test;
   (c) a means for timing intervals associated with performing said pacing unit test;
   (d) a means to generate a set of test signals to be sent to said pacing unit when required for said medical pacing unit test, said means for generating said set of test signals further comprising a microcomputer and a digital/analog converter wherein said microprocessor further comprises a means for generating a series of digital values corresponding to at least one analog test waveform appropriate for said selected medical pacing unit test and a means for transferring said digital values to said digital-/analog converter, said digital/analog converter further including a means for generating at least one corresponding analog test waveform and a means for transferring said analog test waveform to said pacing unit;

(e) a means to analyze a set of pacing signals received by said tester from said pacing unit, wherein said set of pacing signals generated by said pacing unit comprises at least one analog waveform whereupon said means for analyzing further comprises an analog/digital converter for converting said analog waveform to a series of digital values corresponding to said analog waveform, and a microcomputer for analyzing said digital values with programming appropriate to said selected medical pacing unit test; and (f) a means to display result(s) of said analysis;

(g) wherein said means to select said medical pacing unit test includes a means to select a stimulus refractory interval test wherein said means to select said sensed refractory interval test further includes:

(1) a means to generate at least one test waveform and transmit said test waveform to said pacing unit;

(2) a means to determine an interval between a first pacing signal and a second consecutive pacing signal generated by said pacing unit, wherein each of said first and said second pacing signals initially form an analog waveform of a pacing pulse which is converted to proportional digital values by said tester;

(3) a means to control voltage amplitude of said one or more test waveforms;

(4) a means to position said test waveform at a specific interval after generation of a pacing signal generated by said pacing unit;

(5) a means to position a second test waveform at a specific interval after generation of said positioned test waveform of step (4);

(6) a means to measure an interval between said test waveform of step (4) and a next occurring pacing signal after said pacing signal of step (4) of said pacing signals generated by said pacing unit;

(7) a means to compare said interval of step (6) with said interval of step (2), to determine whether said second test waveform of step (5) was sensed by said pacing unit; sensing by said pacing unit being indicated by an increase of said interval of step (6) over said interval of step (2);

(8) a means to repeat steps (4)–(7), continually repositioning said second test waveform of step (5), pursuant to a binary search strategy to calculate an interval when demand circuitry of said pacing unit is first able to sense said second test waveform of step (5).

4. The tester as defined in claim 3, further including a means to repeat said steps (4)–(7) for each positioning of said second test waveform of step (5), to verify the results obtained.

5. A method for quickly and comprehensively testing medical pacing units utilizing a self-contained, portable medical pacing unit tester comprising the steps of:

(a) transferring signals between said tester and said pacing unit which is being tested by said tester;

(b) selecting at least one medical pacing unit test and inputting at least one medical pacing unit parameter where said parameter is necessary to perform said selected medical pacing unit test;

(c) timing intervals associated with performing said pacing unit test;

(d) generating a set of test signals to be sent to said pacing unit when required for said medical pacing unit test, wherein the step of generating said set of test signals includes a microcomputer and a digital-/analog converter, said microprocessor generating a series of digital values corresponding to at least one analog test waveform appropriate for said selected medical pacing unit test and transferring said digital values to said digital/analog converter, said digital/analog converter generating at least one corresponding analog test waveform and transferring said analog test waveform to said pacing unit;

(e) analyzing a set of pacing signals received by said tester and generating from said pacing unit, said set of pacing signals being generated by said pacing unit and comprising at least one analog waveform, said analyzing further comprising the steps of converting said analog waveforms to a series of digital values corresponding to said analog waveform with an analog/digital converter, and analyzing said digital values with a microcomputer by installing on said microcomputer programming appropriate to said selected medical pacing unit test; and (f) displaying result(s) of said analysis;

(g) wherein said selecting step (b) includes a means for selecting a stimulus refractory interval test wherein said stimulus refractory interval test includes:

(1) generating at least one test waveform and transmitting said test waveform to said pacing unit;

(2) determining an interval between successive of said pacing signals generated by said pacing unit, wherein each of said pacing signals initially form an analog waveform of a pacing pulse which is converted to proportional digital values by said tester;

(3) controlling voltage amplitude of said one or more test waveforms;

(4) positioning said test waveform at a specific interval after the generation of one of said pacing signals generated by said pacing unit;

(5) measuring an interval between successive pacing signals generated by said pacing unit, said interval now containing said test waveform of step (4) generated by said tester;

(6) comparing said interval of step (5) with said interval of step (2) to determine whether or not said positioned test waveform was detected by said pacing unit, said detection by said pacing unit being indicated by an increase of said interval of step (5) over said interval of step (2);

(7) repeating steps (4)–(6), continually repositioning said test waveform pursuant to a binary search strategy to calculate an interval after generation of said pacing signals generated by said pacing units when demand circuitry of said pacing unit is first able to sense said test waveform.

6. The method of claim 5, wherein said steps (4)–(6) are repeated at least one time for each positioning of said positioned test waveform to verify the results obtained.

7. A method for quickly and comprehensively testing medical pacing units utilizing a self-contained, portable medical pacing unit tester comprising the steps of:

(a) transferring signals between said tester and said pacing unit which is being tested by said tester;
(b) selecting at least one medical pacing unit test and inputting at least one medical pacing unit parameter where said parameter is necessary to perform said selected medical pacing unit test;
(c) timing intervals associated with performing said pacing unit test;
(d) generating a set of test signals to be sent to said pacing unit when required for said medical pacing unit test, wherein the step of generating said set of test signals includes a microcomputer and a digital/analog converter, said microprocessor generating a series of digital values corresponding to at least one analog test waveform appropriate for said selected medical pacing unit test and transferring said digital values to said digital/analog converter, said digital/analog converter generating at least one corresponding analog test waveform and transferring said analog test waveform to said pacing unit;
(e) analyzing a set of pacing signals received by said tester and generating from said pacing unit, said set of pacing signals being generated by said pacing unit and comprising at least one analog waveform, said analyzing further comprising the steps of converting said analog waveform to a series of digital values corresponding to said analog waveform with an analog/digital converter, and analyzing said digital values with a microcomputer by installing on said microcomputer programming appropriate to said selected medical pacing unit test; and
(f) displaying result(s) of said analysis;
(g) wherein said selecting step (b) includes a means for selecting a sensed refractory interval test wherein said sensed refractory interval test includes:
  (1) generating at least one test waveform and transmitting said test waveform to said pacing unit;
  (2) determining an interval between a first pacing signal and a second consecutive pacing signal generated by said pacing unit, wherein each of said first and said second pacing signals initially forms an analog waveform of a pacing pulse which is converted to proportional digital values by said tester;
  (3) controlling voltage amplitude of said one or more test waveforms;
  (4) positioning said test waveform at a specific interval after the generation of a pacing signal generated by said pacing unit;
  (5) positioning a second test waveform at a specific interval after generation of said positioned test waveform of step (4);
  (6) measuring an interval between said test waveform of step (4) and a next occurring pacing signal after said pacing signal of step (2) generated by said pacing unit;
  (7) comparing said interval of step (6) with said interval of step (2), to determine whether said second test waveform of step (5) was sensed by said pacing unit; sensing by said pacing unit being indicated by an increase of said interval of step (2) over said interval of step (2);
  (8) repeating steps (2)-(7), continually repositioning said second test waveform of step (5), pursuant to a binary search strategy to calculate an interval when demand circuitry of said pacing unit is first able to sense said second test waveform of step (5).

8. The method of claim 7, wherein said steps (4)-(7) are repeated at least one time for each positioning of said second test waveform of step (5), to verify the results obtained.

9. A method for measuring the stimulus refractory period of a medical pacer using an efficient binary search strategy comprising the steps of:
  (a) sensing the occurrence of output pulses from said medical pacer;
  (b) measuring a first interval between successive output pulses of said medical pacer;
  (c) initializing minimum and maximum range variables for the stimulus refractory period to be zero and said first interval, respectively;
  (d) setting a test waveform delay variable equal to said minimum range variable plus one half of the difference between said maximum range variable and said minimum range variable;
  (e) applying a test waveform to said medical pacer following the occurrence of an output pulse of said medical pacer at a delay determined by said test waveform delay variable;
  (f) measuring a second interval between successive output pulses of said medical pacer, said second interval now containing said test waveform;
  (g) comparing said second interval to said first interval to determine if said second interval is greater than said first interval, indicating that said test waveform was sensed by said medical pacer;
  (h) adjusting said minimum and said maximum range variables according to the result of step (g): if said test waveform was sensed, then said maximum range variable is set to said test waveform delay variable, otherwise, said minimum range variable is set to said test waveform delay variable;
  (i) comparing said maximum range variable and said minimum range variable to determine if their difference is equal to or less than a predetermined accuracy value: if so then the stimulus refractory period is reported as the current value of said test waveform delay variable, otherwise, repeat steps (d)-(i).

10. The method as in claim 9, wherein steps (e)-(g) are repeated at least one time during each iteration to verify the comparison of step (g) before proceeding with step (h).

11. A method for measuring the sensed refractory period of a medical pacer using an efficient binary search strategy comprising the steps of:
  (a) sensing the occurrence of output pulses from said medical pacer;
  (b) measuring a first interval between successive output pulses of said medical pacer;
  (c) initializing minimum and maximum range variables for the stimulus refractory period to be zero and said first interval, respectively;
  (d) applying a first test waveform to said medical pacer following the occurrence of an output pulse of said medical pacer at a delay greater than the stimulus refractory period of said medical pacer;
  (e) setting a test waveform delay variable equal to said minimum range variable plus one half of the difference between said maximum range variable and said minimum range variable;
  (f) applying a second test waveform to said medical pacer immediately following the said first test waveform at a delay determined by said test waveform delay variable;

(g) measuring a second interval between said first test waveform and the next successive output pulse of said medical pacer, said second interval now containing said second test waveform;

(h) comparing said second interval to said first interval to determine if said second interval is greater than said first interval, indicating that said second test waveform was sensed by said medical pacer;

(i) adjusting said minimum and said maximum range variables according to the result of step (g): if said second test waveform was sensed, then said maximum range variable is set to said test waveform delay variable, otherwise, said minimum range variable is set to said test waveform delay variable;

(j) comparing said maximum range variable and said minimum range variable to determine if their difference is equal to or less than a predetermined accuracy value: if so then the sensed refractory period is reported as the current value of said test waveform delay variable, otherwise, repeat steps (d)–(j).

12. The method as in claim 11, wherein steps (d)–(h) are repeated at least one time during each iteration to verify the comparison of step (h) before proceeding with step (i).

13. Apparatus for measuring the stimulus refractory period of a medical pacer comprising:

(a) means for sensing the occurrence of output pulses from said medical pacer;

(b) means for measuring a first interval between successive output pulses of said medical pacer;

(c) means for initializing minimum and maximum range variables for the stimulus refractory period to be zero and said first interval, respectively;

(d) means for setting a test waveform delay variable equal to said minimum range variable plus one half of the difference between said maximum range variable and said minimum range variable;

(e) means for producing a test waveform and applying said test waveform to said medical pacer following the occurrence of an output pulse of said medical pacer at a delay determined by said test waveform delay variable;

(f) means for measuring a second interval between successive output pulses of said medical pacer, said second interval now containing said test waveform;

(g) means for comparing said second interval to said first interval to determine if said second interval is greater than said first interval, indicating that said test waveform was sensed by said medical pacer;

(h) means for adjusting said minimum and said maximum range variables according to the result of step (g): if said test waveform was sensed, then said maximum range variable is set to said test waveform delay variable, otherwise, said minimum range variable is set to said test waveform delay variable;

(i) means for comparing said maximum range variable and said minimum range variable to determine if their difference is greater than a predetermined accuracy value;

(j) means to repeat steps (d)–(i) if said difference in step (i) is greater than said predetermined accuracy value;

(k) means to display the current test waveform delay variable as the refractory interval.

14. Apparatus for measuring the sensed refractory period of a medical pacer comprising:

(a) means for sensing the occurrence of output pulses from said medical pacer;

(b) means for measuring a first interval between successive output pulses of said medical pacer;

(c) means for initializing minimum and maximum range variables for the stimulus refractory period to be zero and said first interval, respectively;

(d) means for producing a first test waveform and applying said first test waveform to said medical pacer following the occurrence of an output pulse of said medical pacer at a delay greater than the stimulus refractory period of said medical pacer;

(e) means for setting a test waveform delay variable equal to said minimum range variable plus one half of the difference between said maximum range variable and said minimum range variable;

(f) means for producing a second test waveform and applying said second test waveform to said medical pacer immediately following the said first test waveform at a delay determined by said test waveform delay variable;

(g) means for measuring a second interval between said first test waveform and the next successive output pulse of said medical pacer, said second interval now containing said second test waveform;

(h) means for comparing said second interval to said first interval to determine if said second interval is greater than said first interval, indicating that said second test waveform was sensed by said medical pacer;

(i) means for adjusting either said minimum or said maximum range variables according to the result of step (g): if said second test waveform was sensed, then said maximum range variable is set to said test waveform delay variable, otherwise, said minimum range variable is set to said test waveform delay variable;

(j) means for comparing said maximum range variable and said minimum range variable to determine if their difference is greater than a predetermined accuracy value;

(k) means to repeat steps (d)–(j) if said difference in step (j) is greater than said predetermined accuracy value;

(l) means for displaying the current value of said test waveform delay variable.

* * * * *

UNITED STATES PATENT AND TRADEMARK OFFICE
CERTIFICATE OF CORRECTION

PATENT NO. : 5,209,228

DATED : May 11, 1993

INVENTOR(S) : Gerald G. Cano, Douglas A. Coast, Mark A. Lubinski, Frederick W. Moeller and Timothy F. Rapp It is certified that error appears in the above-identified patent and that said Letters Patent is hereby corrected as shown below:

Cover page, after References Cited, U.S. PATENT DOCUMENTS
"3,757,790 9/1973 Herrmonn ... 128/419 PT" should read
--3,757,790 9/1973 Herrmann ... 128/419 PT--.

Column 10 Line 9 ":" should read --;--.

Column 14 Line 37 "1" should read --160--.

Column 15 Line 34 after "pacemaker" insert --1--.

Column 16 Line 34 after "pacemaker" (second occurrence) insert --1--.

Column 18 Line 64 after "pacemaker" insert --1.--.

Column 21 Line 21 before "present" insert --the--.

Claim 2 Line 46 Column 22 "very" should read --verify--.

Claim 5 Line 22 Column 24 "waveforms" should read --waveform--.

Signed and Sealed this

Twenty-fifth Day of January, 1994

Attest:

BRUCE LEHMAN

*Attesting Officer*  *Commissioner of Patents and Trademarks*